(12) United States Patent
Osaka et al.

(10) Patent No.: US 9,096,578 B2
(45) Date of Patent: Aug. 4, 2015

(54) DIBENZOL[F,H]QUINOXALINE COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Harue Osaka, Kanagawa (JP); Nobuharu Ohsawa, Tochigi (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 309 days.

(21) Appl. No.: 13/663,810

(22) Filed: Oct. 30, 2012

(65) Prior Publication Data
US 2013/0112954 A1    May 9, 2013

(30) Foreign Application Priority Data
Nov. 4, 2011    (JP) .................. 2011-242246

(51) Int. Cl.
H01L 51/50 (2006.01)
C07D 405/14 (2006.01)
C07D 409/04 (2006.01)
C07D 409/14 (2006.01)
H01L 51/00 (2006.01)

(52) U.S. Cl.
CPC ............ C07D 405/14 (2013.01); C07D 409/04 (2013.01); C07D 409/14 (2013.01); H01L 51/0061 (2013.01); H01L 51/0073 (2013.01); H01L 51/0074 (2013.01); H01L 51/0085 (2013.01); H01L 51/5016 (2013.01); H01L 51/5072 (2013.01)

(58) Field of Classification Search
None
See application file for complete search history.

(56) References Cited

U.S. PATENT DOCUMENTS

| 6,723,445 B2 | 4/2004 | Li et al. |
| 7,355,340 B2 | 4/2008 | Shitagaki et al. |
| 2009/0072718 A1 | 3/2009 | Nomura et al. |
| 2009/0140641 A1 | 6/2009 | Nomura et al. |

(Continued)

FOREIGN PATENT DOCUMENTS

| JP | 2007-189001 | 7/2007 |
| JP | 2008-239613 | 10/2008 |

(Continued)

OTHER PUBLICATIONS

Goldsmith, C.R. et al., "C-H Bond Activation by a Ferric Methoxide Complex: Modeling the Rate-Determining Step in the Mechanism of Lipoxygenase," J. Am. Chem. Soc., vol. 124, No. 1, 2002, pp. 83-96.

(Continued)

*Primary Examiner* — Gregory Clark
(74) *Attorney, Agent, or Firm* — Husch Blackwell LLP

(57) ABSTRACT

A novel compound which can be used as a material for a light-emitting element is provided. Specifically, a novel compound is provided which can be suitably used as a material for a light-emitting element where a phosphorescent compound enabling high emission efficiency of the light-emitting element is used as a light-emitting substance. In addition, a novel compound is provided which can be easily synthesized and inexpensively manufactured as well as having the above-described characteristics. A compound is provided in which at least one dibenzothiophenyl group or dibenzofuranyl group is directly bonded to a dibenzo[f,h]quinoxaline skeleton.

20 Claims, 15 Drawing Sheets

(56) References Cited

U.S. PATENT DOCUMENTS

| | | |
|---|---|---|
| 2009/0140642 A1 | 6/2009 | Kadoma et al. |
| 2009/0153041 A1 | 6/2009 | Kawakami et al. |
| 2009/0184633 A1 | 7/2009 | Kadoma et al. |
| 2009/0203704 A1 | 8/2009 | Kadoma et al. |
| 2010/0039024 A1 | 2/2010 | Wendeborn et al. |
| 2010/0249349 A1 | 9/2010 | Chebotareva et al. |
| 2011/0089407 A1 | 4/2011 | Schmidhalter et al. |
| 2011/0210316 A1 | 9/2011 | Kadoma et al. |
| 2012/0193613 A1* | 8/2012 | Kadoma et al. .............. 257/40 |

FOREIGN PATENT DOCUMENTS

| | | |
|---|---|---|
| WO | WO 03/058667 A1 | 7/2003 |
| WO | WO 2004/043937 A1 | 5/2004 |
| WO | WO 2007/090773 A1 | 8/2007 |
| WO | WO 2008/031743 A1 | 3/2008 |
| WO | WO 2009/010091 A1 | 8/2009 |
| WO | WO 2009/100991 A1 | 8/2009 |

OTHER PUBLICATIONS

Onishi.T et al, "A Method of Measuring an Energy Level," *High Molecular EL Materials Development of Light-Emitting High Molecular Compounds*, Kyoritsu Shuppan, Dec. 25, 2004, p. 64-67 (with English translation, pp. 1-3).

European Search Report re application No. EP 11155124.8, dated Jun. 24, 2011.

* cited by examiner

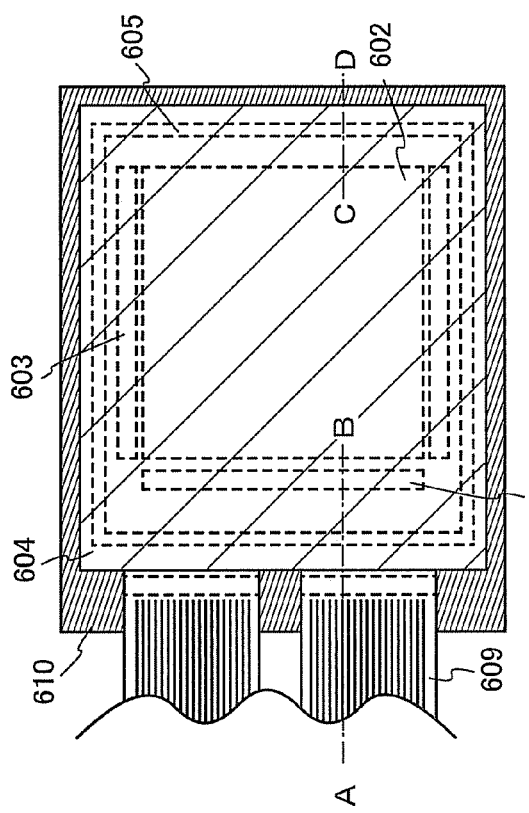
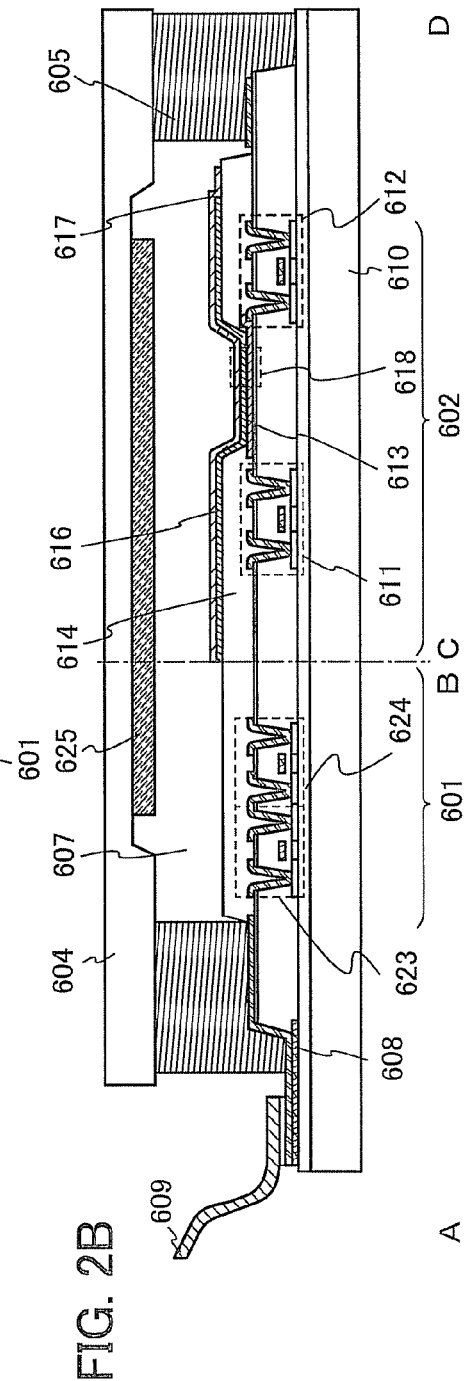
FIG. 2A
FIG. 2B

DIBENZOL[F,H]QUINOXALINE COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a dibenzo[f,h]quinoxaline compound, a light-emitting element, a light-emitting device, an electronic device, and a lighting device.

2. Description of the Related Art

In recent years, research and development have been extensively conducted on light-emitting elements utilizing electroluminescence (EL). In the basic structure of such a light-emitting element, a layer containing a light-emitting substance is interposed between a pair of electrodes. By voltage application to this element, light emission from the light-emitting substance can be obtained.

Such light-emitting elements are self-luminous elements and have advantages over liquid crystal displays in having high pixel visibility and eliminating the need for backlights, for example; thus, such light-emitting elements are thought to be suitable for flat panel display elements. Such light-emitting elements are also highly advantageous in that they can be thin and lightweight. Furthermore, very high speed response is one of the features of such elements.

Since light-emitting layers of such light-emitting elements can be formed in a film form, they make it possible to provide planar light emission. This is a feature difficult to obtain with point light sources typified by incandescent lamps and LEDs or linear light sources typified by fluorescent lamps. Thus, the light-emitting elements also have great potential as planar light sources applicable to lightings and the like.

Light-emitting elements utilizing electroluminescence can be broadly classified according to whether a light-emitting substance is an organic compound or an inorganic compound. In the case of an organic EL element in which a layer containing an organic compound used as a light-emitting substance is provided between a pair of electrodes, application of a voltage between the pair of electrodes causes injection of electrons from a cathode and holes from an anode into the layer containing the organic compound having a light-emitting property and thus a current flows. Recombination of the injected electrons and holes then leads the organic compound having a light-emitting property to its excited state, whereby light emission is obtained from the excited organic compound having a light-emitting property.

The excited state formed by an organic compound can be a singlet excited state or a triplet excited state. Emission from the singlet excited state (S*) is called fluorescence, and emission from the triplet excited state (T*) is called phosphorescence. In addition, the statistical generation ratio thereof in a light-emitting element is considered to be as follows: S*:T*=1:3.

In a compound that emits light from the singlet excited state (hereinafter, referred to as a fluorescent compound), at room temperature, light emission from the triplet excited state (phosphorescence) is not observed while only light emission from the singlet excited state (fluorescence) is observed. Therefore, the internal quantum efficiency (the ratio of generated photons to injected carriers) of a light-emitting element using a fluorescent compound is assumed to have a theoretical limit of 25% based on the ratio of S* to T* which is 1:3.

In contrast, in a compound that emits light from the triplet excited state (hereinafter, referred to as a phosphorescent compound), light emission from the triplet excited state (phosphorescence) is observed. Further, in a phosphorescent compound, since intersystem crossing (i.e., transfer from a singlet excited state to a triplet excited state) easily occurs, the internal quantum efficiency can be increased to 100% in theory. In other words, a light-emitting element using a phosphorescent compound can easily have higher emission efficiency than a light-emitting element using a fluorescent compound. For this reason, light-emitting elements using phosphorescent compounds are now under active development in order to realize highly efficient light-emitting elements.

When a light-emitting layer of a light-emitting element is fowled using a phosphorescent compound described above, in order to suppress concentration quenching or quenching due to triplet-triplet annihilation in the phosphorescent compound, the light-emitting layer is often formed in such a manner that the phosphorescent compound is dispersed in a matrix of another compound. Here, the compound serving as the matrix is called a host material, and the compound dispersed in the matrix, such as the phosphorescent compound, is called a guest material.

When a phosphorescent compound is used as the guest material, one of the properties that the host material needs to have is a triplet level (energy difference between a ground state and a triplet excitation state) higher than that of the phosphorescent compound.

Furthermore, since a singlet level (energy difference between a ground state and a singlet excited state) is generally located higher than a triplet level, a substance that has a high triplet level also has a high singlet level. Therefore, the above substance that has a high triplet level is also effective in a light-emitting element using a fluorescent compound as a light-emitting substance (a guest material).

Studies have been conducted on compounds having dibenzo[f,h]quinoxaline rings, which are examples of the host material used when a phosphorescent compound is a guest material (e.g., see Patent Documents 1 and 2).

REFERENCE

Patent Document

[Patent Document 1] PCT International Publication No. 03/058667
[Patent Document 2] Japanese Published Patent Application No. 2007-189001

SUMMARY OF THE INVENTION

In order that uniform, stable planar light emission is achieved in a light-emitting element using an organic compound, a thin film of the organic compound is preferably amorphous. When crystals are formed partly or entirely in an amorphous thin film, i.e., when what is called crystallization occurs, current flowing between electrodes varies, which makes it difficult to keep the emission efficiency and reliability, as well as hinders uniform planar light emission.

When an organic compound absorbs electrical or optical energy to be in an excited state, the organic compound forms an excimer (an excited dimer) through an interaction with another organic compound in a ground state in some cases. When the excimer is formed, the excited state becomes stable, whereby the singlet level or triplet level of the excimer becomes low as compared to the inherent singlet level or triplet level of the organic compound. In many cases, an organic compound which is readily crystallized easily forms an excimer when in an excited state.

Because a dibenzo[f,h]quinoxaline ring has a planar structure, a dibenzo[f,h]quinoxaline ring is easily crystallized. Owing to the easiness of crystallization, a compound having a dibenzo[f,h]quinoxaline ring easily forms an excimer when in an excited state. The low singlet level or triplet level of the formed excimer may hinder excitation of an objective emission center substance. Further, if crystallization occurs during operation of an element, the film quality change leads to change in carrier balance in some cases. Accordingly, emission efficiency or reliability of the element easily decreases.

Further, in order to obtain a light-emitting device, an electronic device, and a lighting device each having reduced power consumption and high reliability, a light-emitting element having low driving voltage, a light-emitting element having high emission efficiency, or a light-emitting element having a long lifetime has, been demanded. The values of these light-emitting elements can be increased owing to inexpensive manufacture.

Because a dibenzo[f,h]quinoxaline ring has a ring-fused structure, it has a high carrier-transport property. Further, owing to its heterocyclic structure, a dibenzo[f,h]quinoxaline ring is excellent especially in electron-transport property. Moreover, a dibenzo[f,h]quinoxaline ring is a skeleton with a relatively high triplet level. Therefore, with a structure for overcoming the easiness of crystallization, a compound which has a dibenzo[f,h]quinoxaline ring can be suitably used as a host material while maintaining its excellent carrier-transport property.

In view of the above, an object of one embodiment of the present invention is to provide a novel compound which can be used as a material for a light-emitting element. Specifically, an object is to provide a novel compound which can be suitably used as a material for a light-emitting element where a phosphorescent compound enabling high emission efficiency of the light-emitting element is used as a light-emitting substance. In addition, an object is to provide a novel compound which can be easily synthesized and inexpensively manufactured as well as having the above-described characteristics.

Another object of one embodiment of the present invention is to provide a light-emitting element having low driving voltage. A further object of one embodiment of the present invention is to provide a light-emitting element having high emission efficiency. A still further object of one embodiment of the present invention is to provide a light-emitting element having a long lifetime. A yet still further object of one embodiment of the present invention is to provide a light-emitting device, an electronic device, and a lighting device each having reduced power consumption by using the above light-emitting element. A yet still further object of one embodiment of the present invention is to provide a light-emitting device, an electronic device, and a lighting device which are each cost-effective by using the above light-emitting element.

It is only necessary that at least one of the above-described objects be achieved in the present invention.

One embodiment of the present invention is a, compound in which at least one dibenzothiophenyl group or dibenzofuranyl group is directly bonded to a dibenzo[f,h]quinoxaline skeleton.

A compound having a quinoxaline skeleton has a high electron-transport property, and the use of such a compound for a light-emitting element enables the element to have low driving voltage. The compound according to one embodiment of the present invention has a dibenzo[f,h]quinoxaline ring and at least one dibenzothiophene skeleton or dibenzofuran skeleton, thereby easily receiving carriers. Accordingly, the use of the compound as a host material of a light-emitting layer enables manufacture of a light-emitting element with favorable carrier balance in which electrons and holes recombine in the light-emitting layer, thereby allowing the element to have a long lifetime.

Since the dibenzothiophene skeleton or dibenzofuran skeleton is directly bonded to the dibenzo[f,h]quinoxaline ring, a steric structure can be readily formed, and the compound when formed into a film is not easily crystallized. Since crystallization is suppressed, a light-emitting element using the compound can provide uniform and stable planar light emission to have improved reliability and a long lifetime. In addition, a decrease in an excitation level which results from formation of an excimer can be suppressed, so that a decrease in a band gap and a decrease in a $T_1$ level or a $S_1$ level can be prevented. Accordingly, the use of the compound for a light-emitting element enables the element to have high emission efficiency.

Thus, one embodiment of the present invention is a light-emitting element including a dibenzo[f,h]quinoxaline compound in which at least one dibenzothiophenyl group or dibenzofuranyl group is directly bonded to a dibenzo[f,h] quinoxaline skeleton. Note that in the dibenzo[f,h]quinoxaline compound, the 4-position of the dibenzothiophenyl group or the dibenzofuranyl group is preferably bonded to the dibenzo[f,h]quinoxaline skeleton.

One embodiment of the present invention is a dibenzo[f,h] quinoxaline compound represented by General Formula (G1).

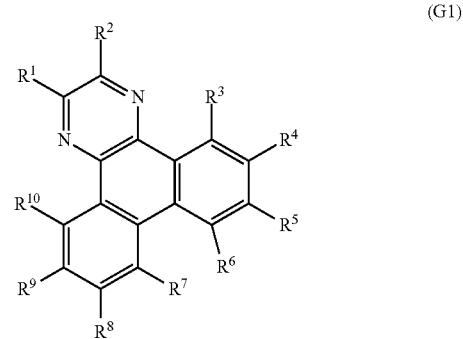

(G1)

In General Formula (G1), any one of $R^1$ to $R^{10}$ represents a substituted or unsubstituted dibenzothiophen-4-yl group or a substituted or unsubstituted dibenzofuran-4-yl group, and the others of $R^1$ to $R^{10}$ separately represent any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a substituted or unsubstituted dibenzothiophen-4-yl group, and a substituted or unsubstituted dibenzofuran-4-yl group.

In General Formula (G1), when one or more of $R^1$ to $R^{10}$ represent a group having a substituent, the substituent is any of an alkyl group having 1 to 6 carbon atoms, a phenyl group, and a biphenyl group. Note that one or more of $R^1$ to $R^{10}$ preferably represent a group having a substituent, in which case the compound represented by General Formula (G1) can have a steric structure and thus crystallization is effectively suppressed.

One embodiment of the present invention is a dibenzo[f,h]quinoxaline compound represented by General Formula (G1).

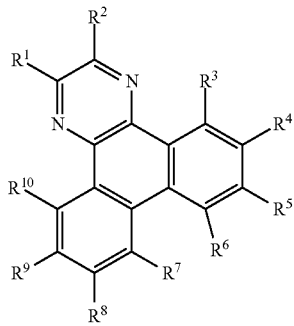

(G1)

In General Formula (G1), any one of $R^1$ to $R^{10}$ represents a group represented by General Formula (G1-1), and the others of $R^1$ to $R^{10}$ separately represent any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, and a group represented by General Formula (G1-2).

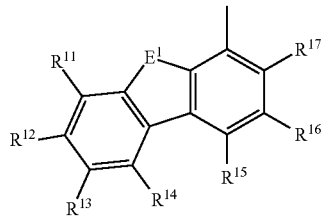

(G1-1)

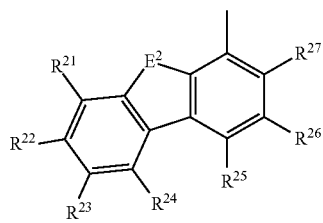

(G1-2)

In General Formula (G1-1), $E^1$ represents sulfur or oxygen, and $R^{11}$ to $R^{17}$ separately represent any of hydrogen, an alkyl group having 1 to 6 carbon atoms, a substituted or unsubstituted phenyl group, and a substituted or unsubstituted biphenyl group. In General Formula (G1-2), $E^2$ represents sulfur or oxygen, and $R^{21}$ to $R^{27}$ separately represent any of hydrogen, an alkyl group having 1 to 6 carbon atoms, a substituted or unsubstituted phenyl group, and a substituted or unsubstituted biphenyl group.

In General Formulae (G1), (G1-1), and (G1-2), when one or more of $R^1$ to $R^{10}$, $R^{11}$ to $R^{17}$, and $R^{21}$ to $R^{27}$ represent a group having a substituent, the substituent is any of an alkyl group having 1 to 6 carbon atoms, a phenyl group, and a biphenyl group. Note that one or more of $R^1$ to $R^{10}$, $R^{11}$ to $R^{17}$, and $R^{21}$ to $R^{27}$ preferably represent a group having a substituent, in which case the compound represented by General Formula (G1) can have a steric structure and thus crystallization is effectively suppressed.

The structure in which the 4-position of the dibenzothiophene skeleton or the dibenzofuran skeleton is bonded to the dibenzo[f,h]quinoxaline skeleton is preferable because with the structure, conjugation is less likely to extend, a band gap between the HOMO level and the LUMO level is wide, and the triplet level and the singlet level are high.

The molecular weight is preferably 450 or more in consideration of stability of film quality. Specifically, it is preferable that one or more of $R^1$ to $R^{10}$, $R^{11}$ to $R^{17}$, and $R^{21}$ to $R^{27}$ be not hydrogen but the other above-described groups which $R^1$ to $R^{10}$, $R^{11}$ to $R^{17}$, and $R^{21}$ to $R^{27}$ can be. In consideration of the case of employing evaporation to form the film, the molecular weight is preferably 1500 or less. In the case where the film formation is performed by a wet process, one or more of $R^1$ to $R^{10}$, $R^{11}$ to $R^{17}$, and $R^{21}$ to $R^{27}$ are preferably an alkyl group or a group having an alkyl group.

For easier synthesis, the groups represented by General Formulae (G1-1) and (G1-2) are preferably the same groups.

One embodiment of the present invention is a dibenzo[f,h]quinoxaline compound represented by General Formula (G2).

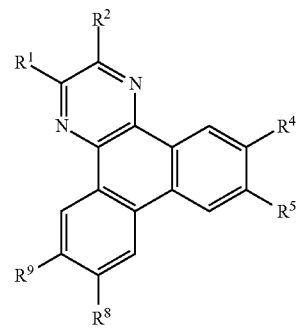

(G2)

In General Formula (G2), any one of $R^1$, $R^2$, $R^4$, $R^5$, $R^8$, and $R^9$ represents a substituted or unsubstituted dibenzothiophen-4-yl group or a substituted or unsubstituted dibenzofuran-4-yl group, and the others of $R^1$, $R^2$, $R^4$, $R^5$, $R^8$, and $R^9$ separately represent any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a substituted or unsubstituted dibenzothiophen-4-yl group, and a substituted or unsubstituted dibenzofuran-4-yl group.

In General Formula (G2), when one or more of $R^1$, $R^2$, $R^4$, $R^5$, $R^8$, and $R^9$ represent a group having a substituent, the substituent is any of an alkyl group having 1 to 6 carbon atoms, a phenyl group, and a biphenyl group. Note that one or more of $R^1$, $R^2$, $R^4$, $R^5$, $R^8$, and $R^9$ preferably represent a group having a substituent, in which case the compound represented by General Formula (G2) can have a steric structure and thus crystallization is effectively suppressed.

One embodiment of the present invention is a dibenzo[f,h]quinoxaline compound represented by General Formula (G2).

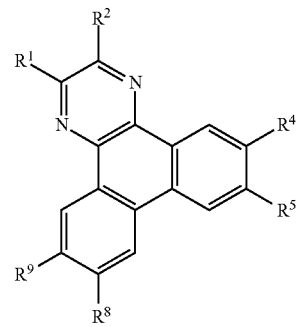

(G2)

In the dibenzo[f,h]quinoxaline compound represented by General Formula (G2), any one of $R^1$, $R^2$, $R^4$, $R^5$, $R^8$, and $R^9$ represents a group represented by General Formula (G1-1), and the others of $R^1$, $R^2$, $R^4$, $R^5$, $R^8$, and $R^9$ separately represent any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, and a group represented by General Formula (G1-2).

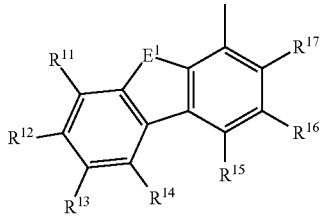

(G1-1)

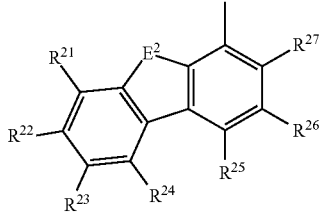

(G1-2)

In General Formula (G1-1), $E^1$ represents sulfur or oxygen, and $R^{11}$ to $R^{17}$ separately represent any of hydrogen, an alkyl group having 1 to 6 carbon atoms, a substituted or unsubstituted phenyl group, and a substituted or unsubstituted biphenyl group. In General Formula (G1-2), $E^2$ represents sulfur or oxygen, and $R^{21}$ to $R^{27}$ separately represent any of hydrogen, an alkyl group having 1 to 6 carbon atoms, a substituted or unsubstituted phenyl group, and a substituted or unsubstituted biphenyl group.

In General Formulae (G2), (G1-1), and (G1-2), when one or more of $R^1$, $R^2$, $R^4$, $R^5$, $R^8$, $R^9$, $R^{11}$ to $R^{17}$, and $R^{21}$ to $R^{27}$ represent a group having a substituent, the substituent is any of an alkyl group having 1 to 6 carbon atoms, a phenyl group, and a biphenyl group. Note that one or more of $R^1$, $R^2$, $R^4$, $R^5$, $R^8$, $R^9$, $R^{11}$ to $R^{17}$, and $R^{21}$ to $R^{27}$ preferably represent a group having a substituent, in which case the compound represented by General Formula (G2) can have a steric structure and thus crystallization is effectively suppressed.

One embodiment of the present invention is a dibenzo[f,h]quinoxaline compound represented by General Formula (G3).

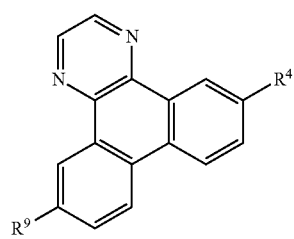

(G3)

In General Formula (G3), one of $R^4$ and $R^9$ represents a substituted or unsubstituted dibenzothiophen-4-yl group or a substituted or unsubstituted dibenzofuran-4-yl group, and the other of $R^4$ and $R^9$ represents any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a substituted or unsubstituted dibenzothiophen-4-yl group, and a substituted or unsubstituted dibenzofuran-4-yl group.

In General Formula (G3), when one or both of $R^4$ and $R^9$ represent a group having a substituent, the substituent is any of an alkyl group having 1 to 6 carbon atoms, a phenyl group, and a biphenyl group. Note that one or both of $R^4$ and $R^9$ preferably represent a group having a substituent, in which case the compound represented by General Formula (G3) can have a steric structure and thus crystallization is effectively suppressed.

One embodiment of the present invention is a dibenzo[f,h]quinoxaline compound represented by General Formula (G3).

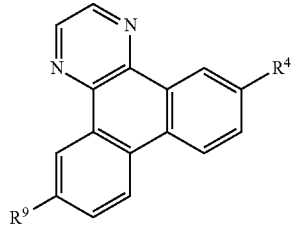

(G3)

In the dibenzo[f,h]quinoxaline compound represented by General Formula (G3), one of $R^4$ and $R^9$ represents a group represented by General Formula (G1-1), and the other of $R^4$ and $R^9$ represents any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, and a group represented by General Formula (G1-2).

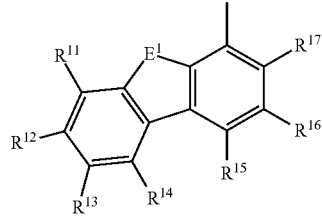

(G1-1)

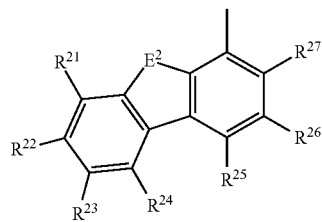

(G1-2)

In General Formula (G1-1), $E^1$ represents sulfur or oxygen, and $R^{11}$ to $R^{17}$ separately represent any of hydrogen, an alkyl group having 1 to 6 carbon atoms, a substituted or unsubstituted phenyl group, and a substituted or unsubstituted biphenyl group. In General Formula (G1-2), $E^2$ represents sulfur or oxygen, and $R^{21}$ to $R^{27}$ separately represent any of hydrogen, an alkyl group having 1 to 6 carbon atoms, a substituted or unsubstituted phenyl group, and a substituted or unsubstituted biphenyl group.

In General Formulae (G3), (G1-1), and (G1-2), when one or more of $R^4$, $R^9$, $R^{11}$ to $R^{17}$, and $R^{21}$ to $R^{27}$ represent a group having a substituent, the substituent is any of an alkyl group having 1 to 6 carbon atoms, a phenyl group, and a biphenyl group. Note that one or more of $R^4$, $R^9$, $R^{11}$ to $R^{17}$, and $R^{21}$ to $R^{27}$ preferably represent a group having a substituent, in which case the compound represented by General Formula (G3) can have a steric structure and thus crystallization is effectively suppressed.

One embodiment of the present invention is a dibenzo[f,h]quinoxaline compound represented by General Formula (G4).

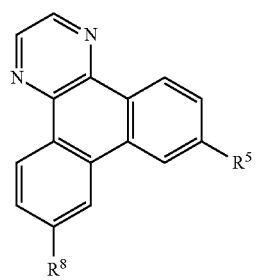

(G4)

In General Formula (G4), one of $R^5$ and $R^8$ represents a substituted or unsubstituted dibenzothiophen-4-yl group or a substituted or unsubstituted dibenzofuran-4-yl group, and the other of $R^5$ and $R^8$ represents any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a substituted or unsubstituted dibenzothiophen-4-yl group, and a substituted or unsubstituted dibenzofuran-4-yl group.

In General Formula (G4), when one or both of $R^5$ and $R^8$ represent a group having a substituent, the substituent is any of an alkyl group having 1 to 6 carbon atoms, a phenyl group, and a biphenyl group. Note that one or both of $R^5$ and $R^8$ preferably represent a group having a substituent, in which case the compound represented by General Formula (G4) can have a steric structure and thus crystallization is effectively suppressed.

One embodiment of the present invention is a dibenzo[f,h]quinoxaline compound represented by General Formula (G4).

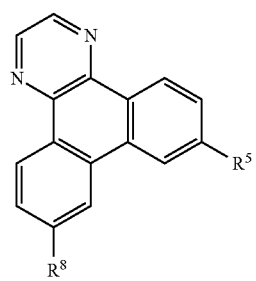

(G4)

In the dibenzo[f,h]quinoxaline compound represented by General Formula (G4), one of $R^5$ and $R^8$ represents a group represented by General Formula (G1-1), and the other of $R^5$ and $R^8$ represents any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, and a group represented by General Formula (G1-2).

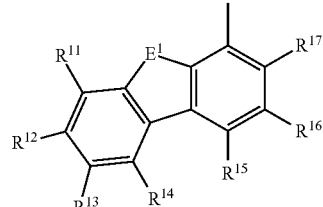

(G1-1)

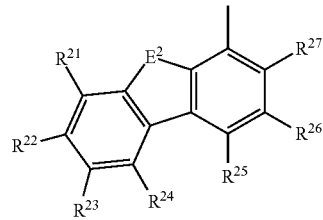

(G1-2)

In General Formula (G1-1), $E^1$ represents sulfur or oxygen, and $R^{11}$ to $R^{17}$ separately represent any of hydrogen, an alkyl group having 1 to 6 carbon atoms, a substituted or unsubstituted phenyl group, and a substituted or unsubstituted biphenyl group. In General Formula (G1-2), $E^2$ represents sulfur or oxygen, and $R^{21}$ to $R^{27}$ separately represent any of hydrogen, an alkyl group having 1 to 6 carbon atoms, a substituted or unsubstituted phenyl group, and a substituted or unsubstituted biphenyl group.

In General Formulae (G4), (G1-1), and (G1-2), when one or more of $R^4$, $R^9$, $R^{11}$ to $R^{17}$, and $R^{21}$ to $R^{27}$ represent a group having a substituent, the substituent is any of an alkyl group having 1 to 6 carbon atoms, a phenyl group, and a biphenyl group. Note that one or more of $R^4$, $R^9$, $R^{11}$ to $R^{17}$, and $R^{21}$ to $R^{27}$ preferably represent a group having a substituent, in which case the compound represented by General Formula (G4) can have a steric structure and thus crystallization is effectively suppressed.

One embodiment of the present invention is a dibenzo[f,h]quinoxaline compound represented by General Formula (G5).

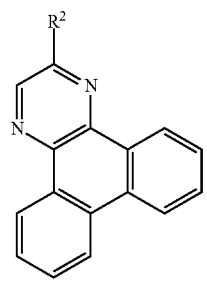

(G5)

In General Formula (G5), $R^2$ represents, a substituted or unsubstituted dibenzothiophen-4-yl group or a substituted or unsubstituted dibenzofuran-4-yl group.

In General Formula (G5), when the dibenzothiophen-4-yl group or the dibenzofuran-4-yl group which is substituted for $R^2$ has a substituent, the substituent is any of an alkyl group having 1 to 6 carbon atoms, a phenyl group, and a biphenyl group. Note that the dibenzothiophen-4-yl group or the dibenzofuran-4-yl group which is substituted for $R^2$ preferably has a substituent, in which case the compound represented by General Formula (G5) can have a steric structure and thus crystallization is effectively suppressed.

One embodiment of the present invention is a dibenzo[f,h]quinoxaline compound represented by General Formula (G5).

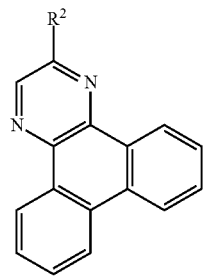

(G5)

In General Formula (G5), $R^2$ represents a group represented by General Formula (G1-1).

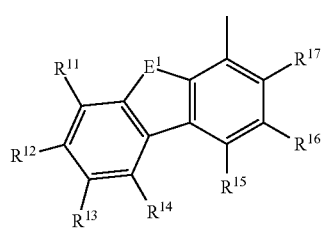

(G1-1)

In General Formula (G1-1), $E^1$ represents sulfur or oxygen, and $R^{11}$ to $R^{17}$ separately represent any of hydrogen, an alkyl group having 1 to 6 carbon atoms, a substituted or unsubstituted phenyl group, and a substituted or unsubstituted biphenyl group.

In General Formulae (G5) and (G1-1), when one or more of $R^2$ and $R^{11}$ to $R^{17}$ represent a group having a substituent, the substituent is any of an alkyl group having 1 to 6 carbon atoms, a phenyl group, and a biphenyl group. Note that one or more of $R^2$ and $R^{11}$ to $R^{17}$ preferably represent a group having a substituent, in which case the compound represented by General Formula (G5) can have a steric structure and thus crystallization is effectively suppressed.

Note that the dibenzo[f,h]quinoxaline compound which has the structure represented by any of General Formulae (G1) to (G5) and in which the group represented by General Formula (G1-1) is a group represented by General Formula (G2-1) and the group represented by General Formula (G1-2) is a group represented by General Formula (G2-2) is industrially advantageous for its high availability of materials and capability of being inexpensively synthesized.

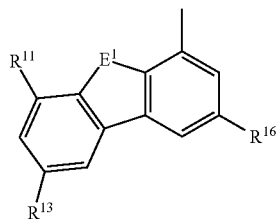

(G2-1)

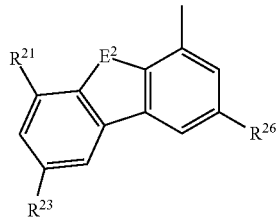

(G2-2)

In General Formula (G2-1), $E^1$ represents sulfur or oxygen, and $R^{11}$, $R^{13}$, and $R^{16}$ separately represent any of hydrogen, an alkyl group having 1 to 6 carbon atoms, a substituted or unsubstituted phenyl group, and a substituted or unsubstituted biphenyl group. In General Formula (G2-2), $E^2$ represents sulfur or oxygen, and $R^{21}$, $R^{23}$, and $R^{26}$ separately represent any of hydrogen, an alkyl group having 1 to 6 carbon atoms, a substituted or unsubstituted phenyl group, and a substituted or unsubstituted biphenyl group.

For easier synthesis, the groups represented by General Formulae (G2-1) and (G2-2) are preferably the same groups.

One embodiment of the present invention is a dibenzo[f,h]quinoxaline compound represented by Structural Formula (100).

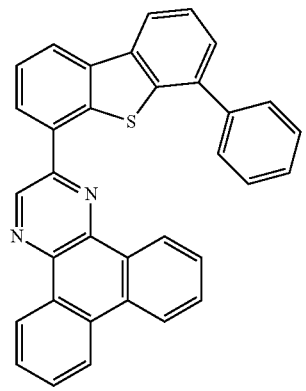

(100)

A structure including a substituent as in the dibenzo[f,h]quinoxaline compound represented by Structural Formula (100), where a phenyl group is bonded to the 4-position of the dibenzothiophene skeleton, is preferable because a compound with the structure can readily have a steric structure and is less likely to be crystallized.

A compound having a quinoxaline skeleton has a high electron-transport property, and the use of such a compound for a light-emitting element enables the element to have low driving voltage. The above dibenzo[f,h]quinoxaline compound has a dibenzo[f,h]quinoxaline ring and at least one dibenzothiophene skeleton or dibenzofuran skeleton, thereby easily receiving carriers, both electrons and holes. Accordingly, the use of the compound as a host material of a light-emitting layer enables manufacture of a light-emitting element in which electrons and holes recombine in the light-emitting layer, thereby allowing the element to have a long lifetime.

Since the dibenzothiophene skeleton or dibenzofuran skeleton is bonded to the dibenzo[f,h]quinoxaline ring, a steric structure can be readily formed, and the compound when formed into a film is not easily crystallized. Since crystallization is suppressed, a light-emitting element using the compound can provide uniform and stable planar light emission. Further, the light-emitting element can have improved reliability and a long lifetime. In addition, a decrease in an excitation level which results from formation of an excimer can be suppressed. Accordingly, the use of the compound for a light-emitting element enables the element to have high emission efficiency.

Furthermore, since the 4-position of the dibenzothiophene skeleton or the dibenzofuran skeleton is directly bonded to the dibenzo[f,h]quinoxaline skeleton in the dibenzo[f,h]quinoxaline compound according to one embodiment of the present invention, the compound can be easily synthesized and inexpensively provided.

Further, one embodiment of the present invention is a light-emitting element including the dibenzo[f,h]quinoxaline compound. Particularly preferred is a light-emitting element including a light-emitting layer between an anode and a cathode, in which the light-emitting layer contains a light-emitting substance and the dibenzo[f,h]quinoxaline compound according to one embodiment of the present invention.

Further preferred is a light-emitting element including a light-emitting layer between an anode and a cathode, in which the light-emitting layer contains a light-emitting substance, an electron-transport compound, and a hole-transport compound. The electron-transport compound is the dibenzo[f,h]quinoxaline compound according to one embodiment of the present invention. The hole-transport compound has a higher hole-transport property than the electron-transport compound and includes a carbazole skeleton, a triarylamine skeleton, a dibenzothiophene skeleton, or a dibenzofuran skeleton.

Here, a layer in contact with the light-emitting layer on the anode side preferably contains the same hole-transport compound as the light-emitting layer.

In the above light-emitting element, a layer in contact with the light-emitting layer on the cathode side preferably contains the dibenzo[f,h]quinoxaline compound according to one embodiment of the present invention.

One embodiment of the present invention is a light-emitting device including the above-described light-emitting element in a light-emitting portion. One embodiment of the present invention is an electronic device including the light-emitting device in a display portion. One embodiment of the present invention is a lighting device including the light-emitting device in a light-emitting portion.

Since the light-emitting element including the dibenzo[f,h]quinoxaline compound according to one embodiment of the present invention has low driving voltage, a light-emitting device with low power consumption can be provided. High emission efficiency of the light-emitting element including the dibenzo[f,h]quinoxaline compound according to one embodiment of the present invention also contributes to low power consumption of the light-emitting device. For a similar reason, an electronic device and a lighting device with low power consumption can be provided by employing one embodiment of the present invention. Further, since a light-emitting element including the dibenzo[f,h]quinoxaline compound according to one embodiment of the present invention has a long lifetime, a light-emitting device, an electronic device, and a lighting device each having high reliability can be provided. In addition, since the dibenzo[f,h]quinoxaline compound can be inexpensively synthesized, the light-emitting device, the electronic device, and the lighting device can be cost-effective.

Note that the light-emitting device in this specification includes an image display device using a light-emitting element. Further, the category of the light-emitting device in this specification includes a module in which a light-emitting element is provided with a connector such as an anisotropic conductive film, TAB (tape automated bonding) tape, or a TCP (tape carrier package); a module in which the top of the TAB tape or the TCP is provided with a printed wiring board; and a module in which an IC (integrated circuit) is directly mounted on a light-emitting element by a COG (chip on glass) method. Furthermore, the category includes light-emitting devices that are used in lighting equipment.

One embodiment of the present invention provides a material for a light-emitting element, specifically a novel dibenzo[f,h]quinoxaline compound which can be suitably used as a host material where a light-emitting substance of a light-emitting layer is dispersed. Another embodiment of the present invention provides a light-emitting element having low driving voltage. A further embodiment of the present invention provides a light-emitting element having high emission efficiency. A still further embodiment of the present invention provides a light-emitting element having a long lifetime. By using the light-emitting element, a still further embodiment of the present invention provides a light-emitting device, an electronic device, and a lighting device each having reduced power consumption. By using the light-emitting element, a still further embodiment of the present invention provides a light-emitting device, an electronic device, and a lighting device which are each cost-effective.

BRIEF DESCRIPTION OF THE DRAWINGS

FIGS. 2A and 2B are conceptual diagrams of an active matrix light-emitting device.

DETAILED DESCRIPTION OF THE INVENTION

Figure 1A:
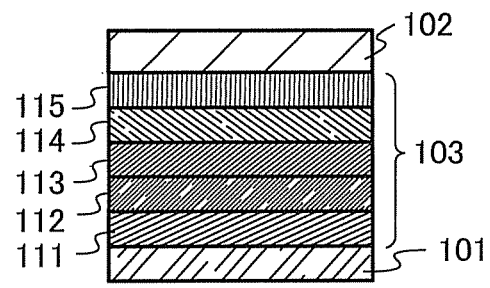
FIGS. 1A and 1B are conceptual diagrams of light-emitting elements.

Hereinafter, embodiments of the present invention will be described in detail with reference to the drawings. Note that the present invention is not limited to the description given below, and it will be easily understood by those skilled in the art that various changes and modifications can be made without departing from the spirit and scope of the present invention. Therefore, the present invention should not be interpreted as being limited to the description of the embodiments given below.

(Embodiment 1)

In this embodiment, a dibenzo[f,h]quinoxaline compound according to one embodiment of the present invention will be described. One embodiment of the present invention is a compound in which at least one dibenzothiophen-4-yl group or dibenzofuran-4-yl group is directly bonded to a dibenzo[f,h]quinoxaline skeleton.

A compound having a quinoxaline skeleton has a high electron-transport property, and the use of such a compound for a light-emitting element enables the element to have low driving voltage. The compound has a dibenzo[f,h]quinoxaline ring and at least one dibenzothiophene skeleton or dibenzofuran skeleton, and either skeleton has a hole-transport property; thus, the compound can easily receive carriers, both electrons and holes. Accordingly, the use of the compound as a host material of a light-emitting layer enables manufacture of a light-emitting element with favorable carrier balance in which electrons and holes recombine in the light-emitting layer, thereby allowing the element to have a long lifetime.

Since the dibenzothiophene skeleton or dibenzofuran skeleton is bonded to the dibenzo[f,h]quinoxaline ring, a steric structure can be readily formed, and the compound when formed into a film is not easily crystallized. Since crystallization is suppressed, a light-emitting element using the compound can provide uniform and stable planar light emission to have improved reliability and a long lifetime. In addition, a decrease in an excitation level due to formation of an excimer, which easily occurs in a molecule having a planar structure, can be suppressed. Accordingly, the use of the compound for a light-emitting element enables the element to have high emission efficiency.

Specifically, since crystallization or a decrease in the triplet level due to formation of an excimer can be suppressed, the compound can be suitably applied to a light-emitting element which uses an emission center substance emitting red to green phosphorescence in spite of having a planar dibenzo[f,h]quinoxaline skeleton. In addition, since the skeleton is excellent in carrier-transport property as already described above, a light-emitting element with low driving voltage can be provided with the use of the dibenzo[f,h]quinoxaline compound described in this embodiment. Moreover, a light-emitting element with a long lifetime can be obtained. That is, the dibenzo[f,h]quinoxaline compound described in this embodiment can be suitably applied to a light-emitting element which uses an emission center substance emitting red to green phosphorescence.

Hereinafter, the dibenzo[f,h]quinoxaline compound in this embodiment will be specifically described. The dibenzo[f,h]quinoxaline compound described in this embodiment is represented by General Formula (G1).

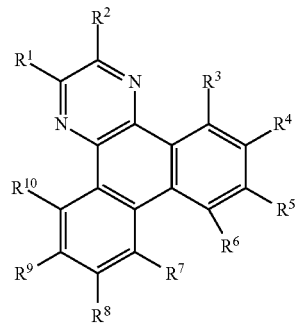

(G1)

In General Formula (G1), any one of $R^1$ to $R^{10}$ represents a substituted or unsubstituted dibenzothiophen-4-yl group or a substituted or unsubstituted dibenzofuran-4-yl group, and the others of $R^1$ to $R^{10}$ separately represent any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a substituted or unsubstituted dibenzothiophen-4-yl group, and a substituted or unsubstituted dibenzofuran-4-yl group.

When $R^3$, $R^6$, $R^7$, and $R^{10}$ in General Formula (G1) are all hydrogen, i.e., when the dibenzo[f,h]quinoxaline compound has the structure represented by General Formula (G2), the dibenzo[f,h]quinoxaline compound can be more inexpensively synthesized and is industrially advantageous owing to its high availability of materials and capability of being easily synthesized.

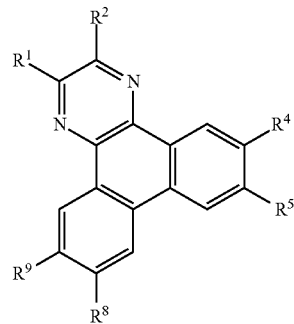

(G2)

In General Formula (G2), any one of $R^1$, $R^2$, $R^4$, $R^5$, $R^8$, and $R^9$ represents a substituted or unsubstituted dibenzothiophen-4-yl group or a substituted or unsubstituted dibenzofuran-4-yl group, and the others of $R^1$, $R^2$, $R^4$, $R^5$, $R^8$, and $R^9$ separately represent any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a substituted or unsubstituted dibenzothiophen-4-yl group, and a substituted or unsubstituted dibenzofuran-4-yl group.

In a similar manner, when $R^1$ to $R^3$, $R^6$ to $R^8$, and $R^{10}$ in General Formula (G1) are all hydrogen, i.e., when the dibenzo[f,h]quinoxaline compound has the structure represented by General Formula (G3), the dibenzo[f,h]quinoxaline compound can be more inexpensively synthesized and is industrially advantageous owing to its high availability of materials and capability of being easily synthesized.

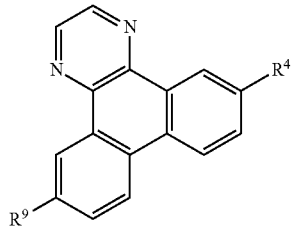

(G3)

In General Formula (G3), one of $R^4$ and $R^9$ represents a substituted or unsubstituted dibenzothiophen-4-yl group or a substituted or unsubstituted dibenzofuran-4-yl group, and the other of $R^4$ and $R^9$ represents any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a substituted or unsubstituted dibenzothiophen-4-yl group, and a substituted or unsubstituted dibenzofuran-4-yl group.

In a similar manner, when $R^1$ to $R^4$, $R^6$, $R^7$, $R^9$, and $R^{10}$ in General Formula (G1) are all hydrogen, i.e., when the dibenzo[f,h]quinoxaline compound has the structure represented by General Formula (G4), the dibenzo[f,h]quinoxaline compound can be more inexpensively synthesized and is industrially advantageous owing to its high availability of materials and capability of being easily synthesized.

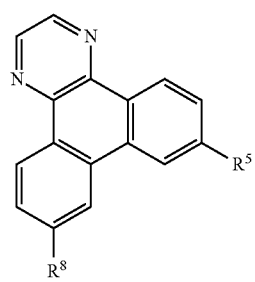

(G4)

In General Formula (G4), one of $R^5$ and $R^8$ represents a substituted or unsubstituted dibenzothiophen-4-yl group or a substituted or unsubstituted dibenzofuran-4-yl group, and the other of $R^5$ and $R^8$ represents any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a substituted or unsubstituted dibenzothiophen-4-yl group, and a substituted or unsubstituted dibenzofuran-4-yl group.

In a similar manner, when $R^1$ and $R^3$ to $R^{10}$ in General Formula (G1) are all hydrogen, i.e., when the dibenzo[f,h] quinoxaline compound has the structure represented by General Formula (G5), the dibenzo[f,h]quinoxaline compound can be more inexpensively synthesized and is industrially advantageous owing to its high availability of materials and capability of being easily synthesized.

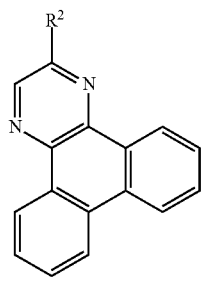

(G5)

In General Formula (G5), $R^2$ represents a substituted or unsubstituted dibenzothiophen-4-yl group or a substituted or unsubstituted dibenzofuran-4-yl group.

In General Formulae (G1) to (G5), when one or more of $R^1$ to $R^{10}$ represent a group having a substituent, the substituent is any of an alkyl group having 1 to 6 carbon atoms, a phenyl group, and a biphenyl group. Note that one or more of $R^1$ to $R^{10}$ preferably represent a group having a substituent, in which case the compound represented by any of General Formulae (G1) to (G5) can have a steric structure and thus crystallization is effectively suppressed.

When at least one of $R^1$ to $R^{10}$ in General Formulae (G1) to (G5) is a substituted or unsubstituted dibenzothiophen-4-yl group or a substituted or unsubstituted dibenzofuran-4-yl group, a steric structure is obtained and crystallization can be suppressed. Since crystallization is suppressed, a light-emitting element using the dibenzo[f,h]quinoxaline compound can provide uniform and stable planar light emission to have improved reliability and a long lifetime. In addition, since the steric structure is obtained, formation of an excimer can be suppressed, so that a decrease in an excitation level which results from the formation of an excimer can be suppressed; therefore, the dibenzo[f,h]quinoxaline compound can be suitably used in a light-emitting element which uses a light-emitting substance emitting red to green phosphorescence.

The above dibenzothiophen-4-yl group and dibenzofuran-4-yl group can be represented by General Formula (G1-1) or (G1-2).

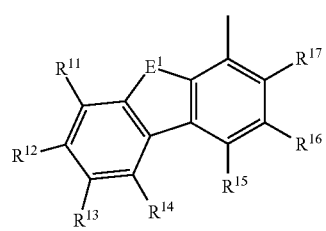

(G1-1)

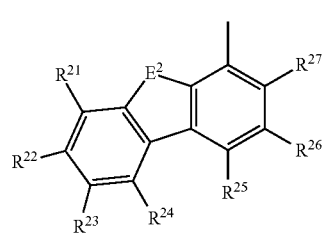

(G1-2)

In General Formula (G1-1), $E^1$ represents sulfur or oxygen, and $R^{11}$ to $R^{17}$ separately represent any of hydrogen, an alkyl group having 1 to 6 carbon atoms, a substituted or unsubstituted phenyl group, and a substituted or unsubstituted biphenyl group. In General Formula (G1-2), $E^2$ represents sulfur or oxygen, and $R^{21}$ to $R^{27}$ separately represent any of hydrogen, an alkyl group having 1 to 6 carbon atoms, a substituted or unsubstituted phenyl group, and a substituted or unsubstituted biphenyl group. It is preferable that $R^{11}$ to $R^{17}$ and $R^{21}$ to $R^{27}$ be comparatively large groups such as a phenyl group or a biphenyl group because in that case, crystallization can be further suppressed. Particularly preferred is a phenyl group, which is unlikely to cause a decrease in a band gap and a decrease in the triplet level.

In General Formulae (G1-1) and (G1-2), when one or more of $R^{11}$ to $R^{17}$ and $R^{21}$ to $R^{27}$ represent a group having a substituent, the substituent is any of an alkyl group having 1 to 6 carbon atoms, a phenyl group, and a biphenyl group. Note that one or more of $R^{11}$ to $R^{17}$ and $R^{21}$ to $R^{27}$ preferably represent a group having a substituent, in which case the compound represented by any of General Formulae (G1) to (G5) can have a more steric structure and thus crystallization or excimer formation is effectively suppressed.

When $R^{12}$, $R^{14}$, $R^{15}$, and $R^{17}$ in General Formula (G1-1) and $R^{22}$, $R^{24}$, $R^{25}$, and $R^{27}$ in General Formula (G1-2) are all hydrogen, i.e., when the dibenzo[f,h]quinoxaline compound has the group represented by General Formula (G2-1) or (G2-2), the dibenzo[f,h]quinoxaline compound can be more inexpensively synthesized and is industrially advantageous owing to its high availability of materials and capability of being easily synthesized.

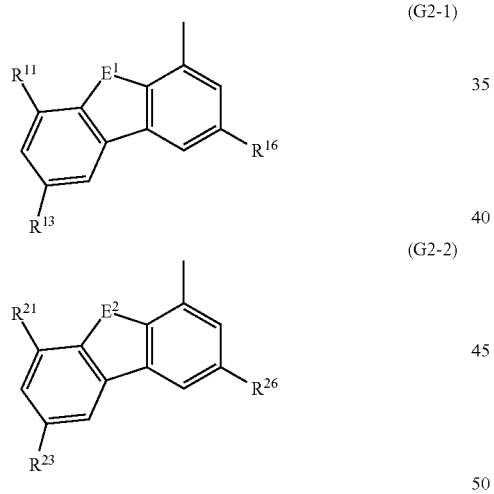

In General Formula (G2-1), $E^1$ represents sulfur or oxygen, and $R^{11}$, $R^{13}$, and $R^{16}$ separately represent any of hydrogen, an allyl group having 1 to 6 carbon atoms, a substituted or unsubstituted phenyl group, and a substituted or unsubstituted biphenyl group. In General Formula (G2-2), $E^2$ represents sulfur or oxygen, and $R^{11}$, $R^{13}$, and $R^{16}$ separately represent any of hydrogen, an alkyl group having 1 to 6 carbon atoms, a substituted or unsubstituted phenyl group, and a substituted or unsubstituted biphenyl group.

In General Formulae (G2-1) and (G2-2), when one or more of $R^{11}$, $R^{13}$, $R^{16}$, $R^{21}$, $R^{23}$, and $R^{26}$ represent a group having a substituent, the substituent is any of an alkyl group having 1 to 6 carbon atoms, a phenyl group, and a biphenyl group. Note that one or more of $R^{11}$, $R^{13}$, $R^6$, $R^{21}$, $R^{23}$, and $R^{26}$ preferably represent a group having a substituent, in which case the compound represented by any of General Formulae (G1) to (G5) can have a more steric structure and thus crystallization or excimer formation is effectively suppressed.

Specific examples of the dibenzo[f,h]quinoxaline compounds represented by General Formulae (G1) to (G5) are dibenzo[f,h]quinoxaline compounds represented by Structural Formulae (100) to (110), (120) to (123), and (130) to (133). However, the present invention is not limited to these compounds.

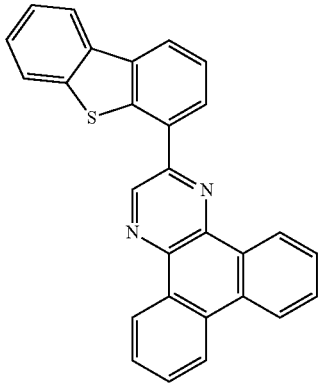

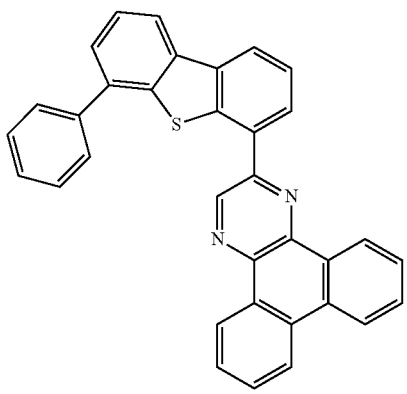

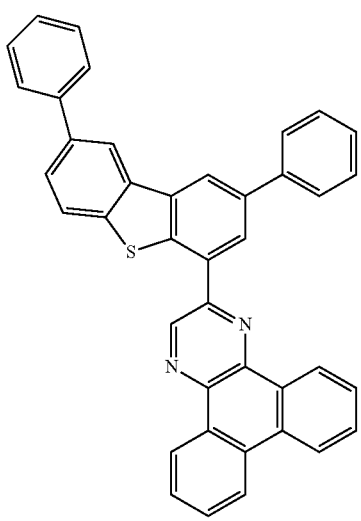

-continued
(103)
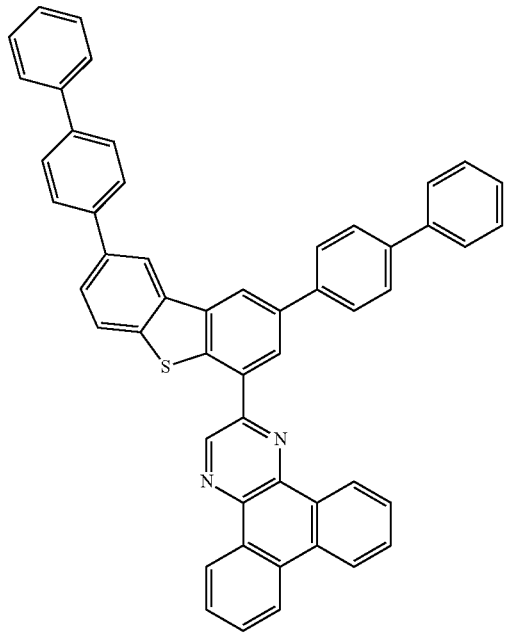
(104)
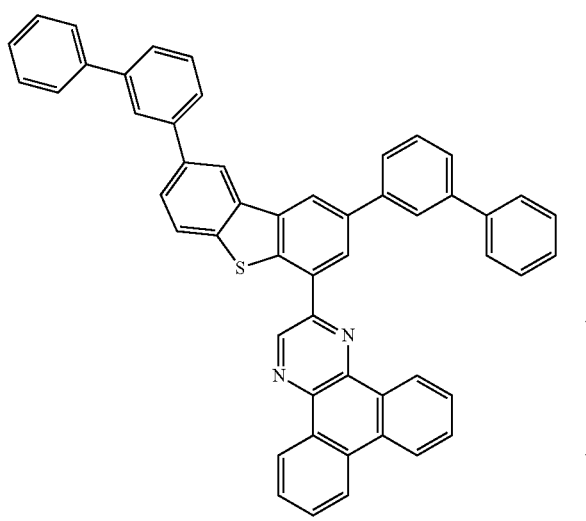
(105)
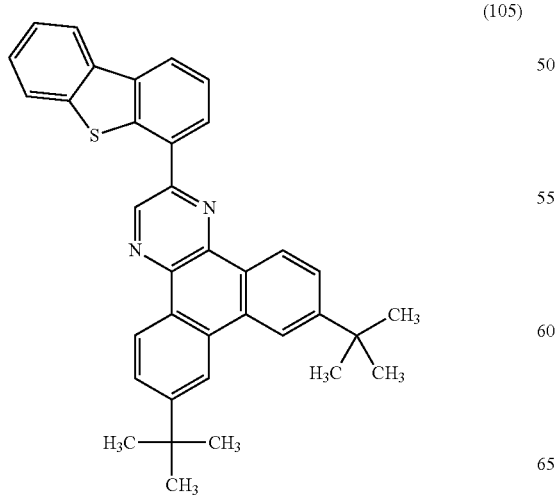
-continued
(106)
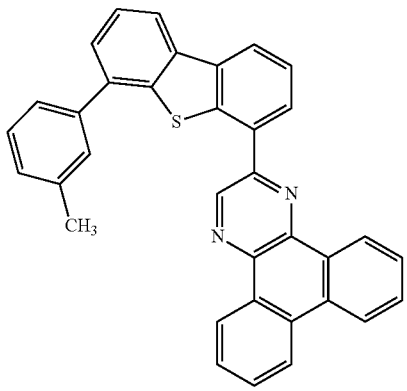
(107)
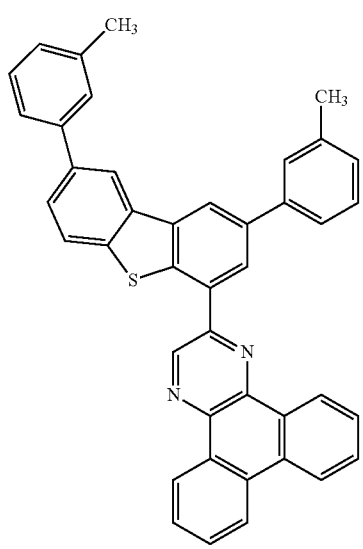
(108)
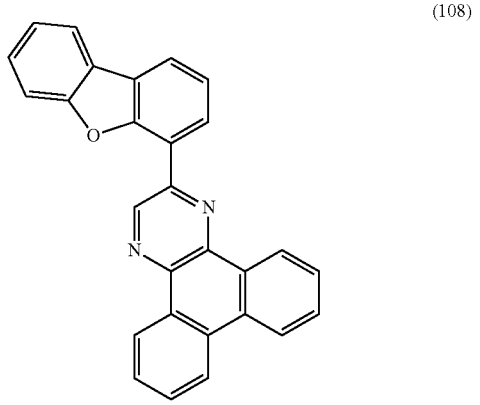

(109)
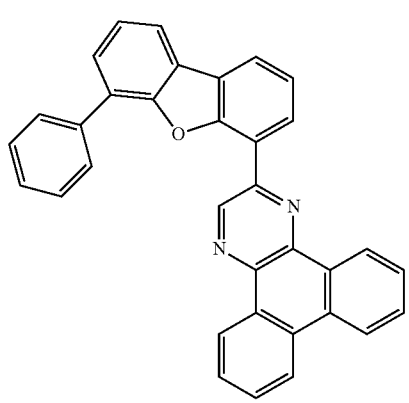
(110)
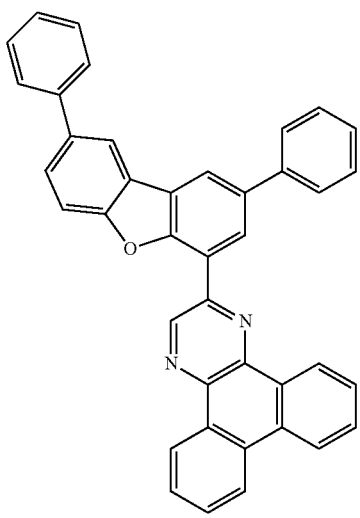
(120)
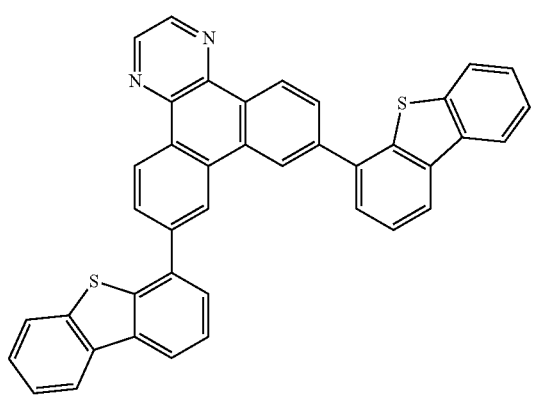
(121)
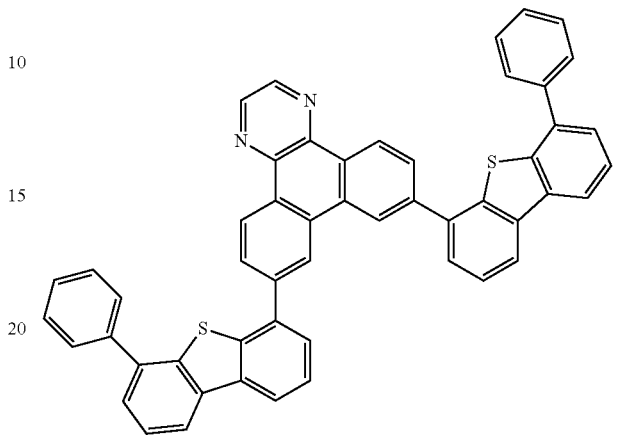
(122)
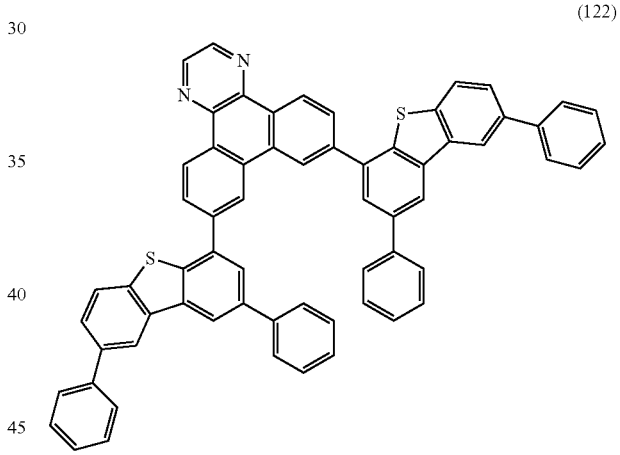
(123)
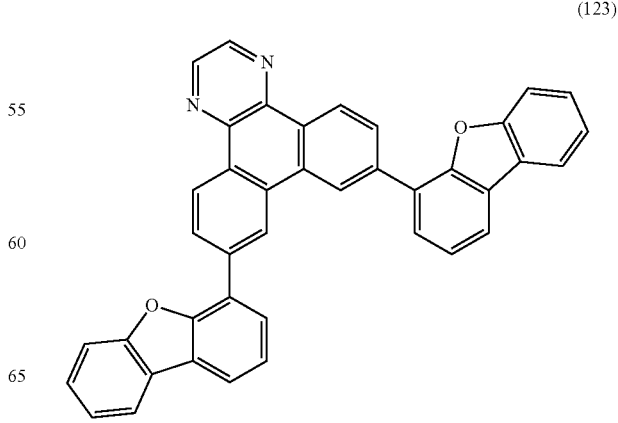

(130)

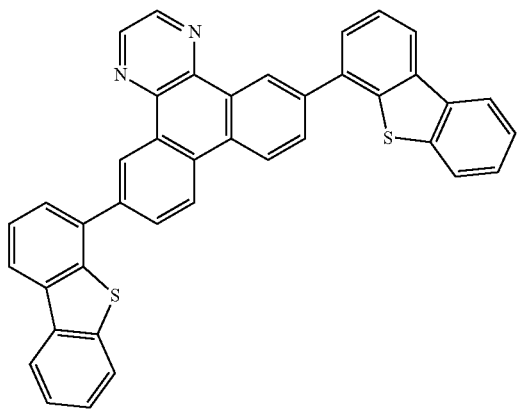

(131)

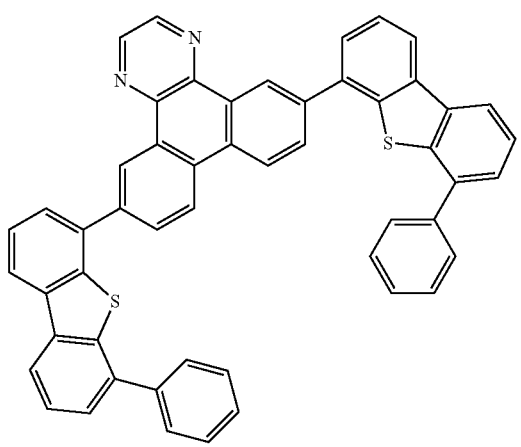

(132)

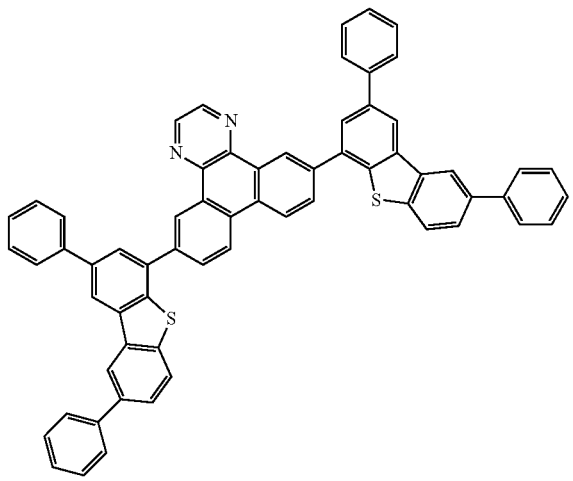

(133)

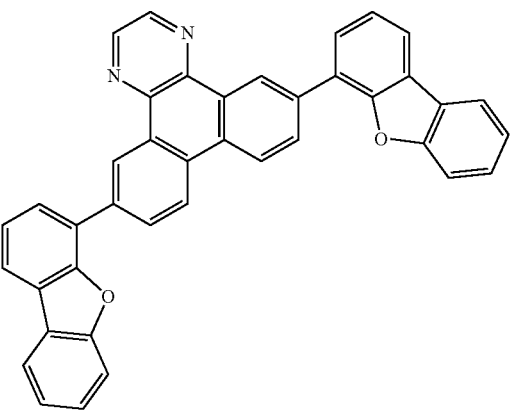

A variety of reactions can be applied to a method of synthesizing the dibenzo[/h]quinoxaline compound according to one embodiment of the present invention. For example, synthesis reactions described below enable the synthesis of the dibenzo[f,h]quinoxaline compound according to one embodiment of the present invention, represented by General Formula (G1). Note that the method of synthesizing the dibenzo[f,h]quinoxaline compound according to one embodiment of the present invention is not limited to the following synthesis method.

<<Method of Synthesizing Dibenzoquinoxaline Compound Represented by General Formula (G1)>>

As shown in Synthesis Scheme (A-1), the dibenzo[f,h]quinoxaline compound represented by General Formula (G1) can be synthesized by coupling a halogenated dibenzoquinoxaline compound (a1) and a dibenzothiophene-4-boron compound or a dibenzofuran-4-boron compound (a2). Synthesis Scheme (A-1) is shown below.

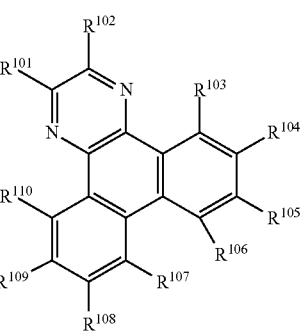

(a1)
dibenzothiophene-4-boron compound
or
dibenzofuran-4-boron compound
(a2)

coupling ⟶

(A-1)

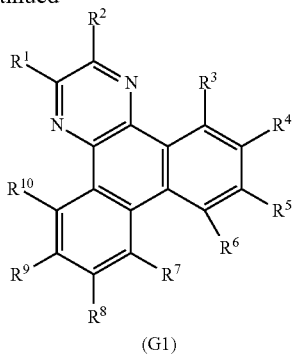

(G1)

Any one of $R^{101}$ to $R^{110}$ of Compound (a1) represents a halogeno group and the others of $R^{101}$ to $R^{110}$ separately represent any of a halogeno group, hydrogen, an allyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, and a substituted or unsubstituted triphenylenyl group. The halogeno group is any of iodine, bromine, and chlorine, which are preferred in descending order of reactivity. As examples of the boron group of Compound (a2), a boronic acid group and a dialkoxyboron group can be given.

Note that in Synthesis Scheme (A-1), a bond is formed between the carbon to which the halogeno group of Compound (a1) is bonded and the carbon to which the boron group of Compound (a2) is bonded.

Note that any of a variety of reactions can be employed for the coupling reaction in Synthesis Scheme (A-1). As an example, a synthesis method using a metal catalyst in the presence of a base can be given. Specifically, a Suzuki-Miyaura reaction can be employed.

Note that when two or more of $R^1$ to $R^{10}$ represent a substituted or unsubstituted dibenzothiophen-4-yl groups or a substituted or unsubstituted dibenzofuran-4-yl group in General Formula (G1) and the bonded substituents are the same substituents, the synthesis can be facilitated by making the substituents undergo the coupling reaction at the same time.

The dibenzo[f,h]quinoxaline compound in this embodiment has a wide band gap, a high singlet level, and a high triplet level; thus, when the dibenzo[f,h]quinoxaline compound is used for a host material in a light-emitting layer of a light-emitting element, in which a light-emitting substance is dispersed, the light-emitting element can have high emission efficiency. In particular, the dibenzo[f,h]quinoxaline compound is suitably used as a host material in which a phosphorescent compound is dispersed. Further, since the dibenzo[f,h]quinoxaline compound in this embodiment are substances having a high electron-transport property, the dibenzo[f,h]quinoxaline compound can be suitably used as a material for an electron-transport layer in a light-emitting element. With the use of the dibenzo[f,h]quinoxaline compound in this embodiment, it is possible to obtain a light-emitting element having low driving voltage. In addition, it is possible to obtain a light-emitting element having high emission efficiency. A light-emitting element having a long lifetime can also be obtained. Furthermore, with the use of this light-emitting element, a light-emitting device, an electronic device, and a lighting device each having reduced power consumption can be obtained.

Note that the dibenzo[f,h]quinoxaline compound according to one embodiment of the present invention can also be used in an organic thin film solar battery. More specifically, the dibenzo[f,h]quinoxaline compound can be used in a carrier-transport layer or a carrier-injection layer since the dibenzo[f,h]quinoxaline compound has a carrier-transport property. The dibenzo[f,h]quinoxaline compound can be photoexcited and hence can be used for a power generation layer.

(Embodiment 2)

In this embodiment, a detailed example of the structure of the light-emitting element which uses the dibenzo[f,h]quinoxaline compound in Embodiment 1 is described below with reference to FIG. 1A.

A light-emitting element in this embodiment includes a plurality of layers between a pair of electrodes. In this embodiment, the light-emitting element includes a first electrode 101, a second electrode 102, and an EL layer 103, which is provided between the first electrode 101 and the second electrode 102. Note that in this embodiment, the first electrode 101 functions as an anode and the second electrode 102 functions as a cathode. In other words, when a voltage is applied between the first electrode 101 and the second electrode 102 so that the potential of the first electrode 101 is higher than that of the second electrode 102, light emission can be obtained. A light-emitting element in this embodiment is a light-emitting element in which the dibenzo[f,h]quinoxaline compound is used for any of layers in the EL layer 103.

For the first electrode 101, any of metals, alloys, electrically conductive compounds, and mixtures thereof which have a high work function (specifically, a work function of 4.0 eV or more) or the like is preferably used. Specifically, for example, indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like can be given. Films of these electrically conductive metal oxides are usually formed by a sputtering method but may be formed by application of a sol-gel method or the like. For example, a film of indium oxide-zinc oxide can be formed by a sputtering method using a target obtained by adding 1 wt % to 20 wt % of zinc oxide to indium oxide. Further, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Besides, gold (Au), platinum (Pt), nickel (Ni), tungsten (W), chromium (Cr), molybdenum (Mo), iron (Fe), cobalt (Co), copper (Cu), palladium (Pd), nitrides of metal materials (e.g., titanium nitride), and the like can be given. Graphene can also be used.

There is no particular limitation on a stacked structure of the EL layer 103. The EL layer 103 can be formed by combining a layer that contains a substance having a high electron-transport property, a layer that contains a substance having a high hole-transport property, a layer that contains a substance having a high electron-injection property, a layer that contains a substance having a high hole-injection property, a layer that contains a bipolar substance (a substance having a high electron-transport and hole-transport property), and the like as appropriate. For example, the EL layer 103 can be formed by combining a hole-injection layer, a hole-transport layer, a light-emitting layer, an electron-transport layer, an electron-injection layer, and the like as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the first electrode 101. Materials included in the layers are specifically given below.

The hole-injection layer 111 is a layer containing a substance having a high hole-injection property. Molybdenum oxide, vanadium oxide, ruthenium oxide, tungsten oxide, manganese oxide, or the like can be used. Alternatively, the hole-injection layer 111 can be formed with a phthalocyanine-based compound such as phthalocyanine (abbreviation: H₂Pc) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), a high molecular compound such as poly(ethylenedioxythiophene)/poly(styrenesulfonic acid) (PEDOT/PSS), or the like.

Alternatively, a composite material in which a substance having a high hole-transport property contains a substance having an acceptor property can be used for the hole-injection layer 111. Note that the use of such a substance having a high hole-transport property which contains a substance having an acceptor property enables selection of a material used to form an electrode regardless of its work function. In other words, besides a material having a high work function, a material having a low work function can also be used for the first electrode 101. As the substance having an acceptor property, 7,7,8,8-tetracyano-2,3,5,6-tetrafluoroquinodimethane (abbreviation: F₄-TCNQ), chloranil, and the like can be given. In addition, transition metal oxides can be given. Oxides of the metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable in that their electron-accepting property is high. Among these, molybdenum oxide is especially preferable in that it is stable in the air, has a low hygroscopic property, and is easily treated.

As the substance having a high hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $1 \times 10^{-6}$ cm²/Vs or more is preferably used. Further, other than these substances, any substance that has a property of transporting more holes than electrons may be used. Organic compounds that can be used as the substance having a high hole-transport property in the composite material are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-dipheny-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivatives that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole derivatives that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbons that can be used for the composite material are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. As these aromatic hydrocarbons given here, it is preferable that an aromatic hydrocarbon having a hole mobility of $1 \times 10^{-6}$ cm²/Vs or more and having 14 to 42 carbon atoms be used.

Note that the aromatic hydrocarbons that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine](abbreviation: poly-TPD) can also be used.

The hole-transport layer 112 is a layer that contains a substance having a high hole-transport property. Examples of the substance having a high hole-transport property are aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), and the like. The substances mentioned here are mainly ones that have a hole mobility of $1 \times 10^{-6}$ cm²/Vs or more. An organic compound given as an example of the substance having a high hole-transport property in the composite material described above can also be used for the hole-transport layer 112. A high molecular compound such as poly(N-vinylcarbazole) (abbreviation: PVK) or poly(4-vinyltriphenylamine) (abbreviation: PVTPA) can also be used. However, other than these substances, any substance that has a property of transporting more holes than electrons may be used. Note that the layer that contains a substance having a high hole-transport property is not limited to a single layer, and may be a stack of two or more layers including any of the above substances.

The light-emitting layer 113 is a layer containing a light-emitting substance. The light-emitting layer 113 may be formed with a film containing only a light-emitting substance or a film in which an emission center substance is dispersed in a host material.

There is no particular limitation on a material that can be used as the light-emitting substance or the emission center substance in the light-emitting layer 113, and light emitted from the material may be either fluorescence or phosphorescence. Examples of the above light-emitting substance or emission center substance are the following substances: fluorescent substances such as N,N'-bis[4-(9-phenyl-9H-fluoren-9-yl)phenyl]-N,N'-diphenyl-pyrene-1,6-diamine (abbreviation: 1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl) triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine](abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'', N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM); and phosphorescent substances such as bis[2-(3',5'-bistrifluoromethylphenyl)pyridinato-N,$C^{2'}$]iridium(III) picolinate (abbreviation: Ir(CF$_3$ ppy)$_2$(pic)), bis[2-(4',6'-difluorophenyl)pyridinato-N,$C^{2'}$]iridium(II) acetylacetonate (abbreviation: FIracac), tris(2-phenylpyridinato-N,$C^{2'}$)iridium(III) (abbreviation: Ir(ppy)$_3$), bis(2-phenylpyridinato-N,$C^{2'}$)iridium(III) acetylacetonate (abbreviation: Ir(ppy)$_2$acac), bis(1,2-diphenyl-1H-benzimidazolato)iridium(III) acetylacetonate (abbreviation: Ir(pbi)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), bis(2,4-diphenyl-1,3-oxazolato-N,$C^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,$C^2$)iridium(III) acetylacetonate (abbreviation: Ir(bt)$_2$(acac)), (acetylacetonato)bis[2,3-bis(4-fluorophenyl)-5-methylpyrazinato]iridium(III) (abbreviation: Ir(Fdppr-Me)$_2$(acac)), (acetylacetonato)bis[2-(4-methoxyphenyl)-3,5-dimethylpyrazinato]iridium(III) (abbreviation: Ir(dmmoppr)$_2$(acac)), tris(2-phenylquinolinato-N,$C^{2'}$)iridium(III) (abbreviation: Ir(pq)$_3$), bis(2-phenylquinolinato-N, $C^2$)iridium(III)(acetylacetonate) (abbreviation: Ir(pq)$_2$(acac)), (acetylacetonato)bis(3,5-dimethyl-2-phenylpyrazinato)iridium(III) (abbreviation: Ir(mppr-Me)$_2$ (acac)), (acetylacetonato)bis(5-isopropyl-3-methyl-2-phenylpyrazinato)iridium(III) (abbreviation: Ir(mppr-iPr)$_2$ (acac)), bis[2-(2'-benzo[4,5-α]thienyl)pyridinato-N,$C^{3'}$] iridium(III)(acetylacetonate) (abbreviation: Ir(btp)$_2$(acac)), bis(1-phenylisoquinolinato-N,$C^{2'}$)iridium(III) acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$ (acac)]), bis(2,3,5-triphenylpyrazinato) (dipivaloylmethanato)iridium(III) (abbreviation: [Ir(tppr)$_2$ (dpm)]), (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(1H) (abbreviation: [Ir(dppm)$_2$(acac)]), 2,3,7,8,12,13,17,18-octaethyl-21H,23H-porphine platinum(II) (abbreviation: PtOEP), tris(acetylacetonato) (monophenanthroline)terbium (III) (abbreviation: [Tb(acac)$_3$(Phen)]), tris(1,3-diphenyl-1,3-propanedionato) (monophenanthroline)europium(III) (abbreviation: [Eu(DBM)$_3$(Phen)]), and tris[1-(2-thenoyl)-3,3,3-trifluoroacetonato](monophenanthroline)europium(III) (abbreviation: [Eu(TTA)$_3$(Phen)]). Note that the dibenzo[f,h]quinoxaline compound described in Embodiment 1 can also be used as a light-emitting substance or an emission center substance. The dibenzoL[h]quinoxaline compound is an emission center substance which emits light having a spectrum in a range from purple to green.

Although there is no particular limitation on a material that can be used as the host material described above, any of the following substances can be used for the host material, for example: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc (II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-

1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo[g,p]chrysene derivatives can be given, and specific examples are 9,10-diphenylanthracene (abbreviation: DPAnth), N,N-diphenyl-9-[4-(10-phenyl-9-anthryl)phenyl]-9H-carbazol-3-amine (abbreviation: CzAlPA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenyl-chrysene, N,N,N',N',N",N",N'",N'"-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbere-4,4'-diyl)diphenanthrene (abbreviation: DPNS2), 3,3',3"-(benzene-1,3,5-triyl)tripyrene (abbreviation: TPB3), and the like. Further, the dibenzo[f,h]quinoxaline compound described in Embodiment 1 can also be suitably used as the host material. One or more substances having a wider band gap than the emission center substance described above may be selected from these substances and known substances. Moreover, in the case where the emission center substance is a substance which emits phosphorescence, a substance having a higher triplet level (energy difference between a ground state and a triplet excitation state) than the emission center substance can be selected as the host material. In the case where the emission center substance is a substance which emits fluorescence, in a similar manner, a substance having a higher singlet level (energy difference between a ground state and a singlet excitation state) than the emission center substance can be selected as the host material.

Note that a light-emitting element which uses the dibenzo[f,h]quinoxaline compound in Embodiment 1 as a host material can have high emission efficiency since the dibenzo[f,h]quinoxaline compound has a high singlet level and a high triplet level and is unlikely to form an excimer. In addition, the excellent electron-transport property of the dibenzo[f,h]quinoxaline compound allows the light-emitting element to be driven at low voltage. The light-emitting element can also have a long lifetime since the dibenzo[f,h]quinoxaline compound is not easily crystallized and can easily receive carriers, both electrons and holes. The dibenzo[f,h]quinoxaline compound can be suitably used in a light-emitting element whose emission center substance is a substance which emits green to red phosphorescence (phosphorescence with a wavelength longer than or equal to that of green light). The reason for this is that the high triplet level of the dibenzo[f,h]quinoxaline compound allows a substance which emits green to red phosphorescence to be effectively excited, so that a light-emitting element with high emission efficiency can be easily provided.

The dibenzo[f,h]quinoxaline compound described in Embodiment 1 has a dibenzothiophene skeleton or a dibenzofuran skeleton in addition to a dibenzo[f,h]quinoxaline ring, thereby easily receiving holes. Accordingly, by the use of the compound as a host material of a light-emitting layer, electrons and holes recombine in the light-emitting layer, so that it is possible to suppress the decrease in the lifetime of the light-emitting element. Furthermore, the introduction of the dibenzothiophene skeleton or the dibenzofuran skeleton enables the compound to have a three-dimensionally bulky structure, and the compound is not easily crystallized when formed into a film. By the use of the compound for a light-emitting element, the element can have a long lifetime. In addition, owing to its three-dimensionally bulky structure, the dibenzo[f,h]quinoxaline compound is unlikely to form an excimer, thereby preventing a decrease in an excitation level due to formation of an excimer and thus enabling the light-emitting element to have high emission efficiency.

The dibenzo[f,h]quinoxaline skeleton predominantly determines the LUMO level of the compound in which the dibenzothiophene skeleton or the dibenzofuran skeleton is bonded to the dibenzo[f,h]quinoxaline ring. Further, the compound has a deep LUMO level of at least −2.8 eV or less, specifically −2.9 eV or less on the basis of cyclic voltammetry (CV) measurements. For example, 2-(6-phenyldibenzothiophen-4-yl)dibenzo[f,h]quinoxaline (abbreviation: 2DBTDBq-IV), which is one of the dibenzo[f,h]quinoxaline compounds described in Embodiment 1, has a LUMO level of −2.99 eV on the basis of the CV measurements. Furthermore, the LUMO level of a phosphorescent compound having a diazine skeleton, which is typified by the above-described phosphorescent compound having a pyrazine skeleton, such as [Ir(mppr-Me)$_2$(acac)], [Ir(mppr-iPr)$_2$(acac)], [Ir(tppr)$_2$(acac)], or [Ir(tppr)$_2$(dpm)] or the above-described phosphorescent compound having a pyrimidine skeleton such as [Ir(tBuppm)$_2$(acac)] or [Ir(dppm)$_2$(acac)], is substantially as deep as the LUMO level of the dibenzo[f,h]quinoxaline compound. Therefore, when a light-emitting layer includes the dibenzo[f,h]quinoxaline compound described in Embodiment 1 as a host material and a phosphorescent compound having a diazine skeleton (particularly a pyrazine skeleton or a pyrimidine skeleton) as a guest material, traps for electrons in the light-emitting layer can be reduced to a minimum, and extremely low driving voltage can be achieved.

Note that the light-emitting layer 113 can also be a stack of two or more layers. For example, in the case where the light-emitting layer 113 is formed by stacking a first light-emitting layer and a second light-emitting layer in that order over the hole-transport layer, a substance having a hole-transport property is used for the host material of the first light-emitting layer and a substance having an electron-transport property is used for the host material of the second light-emitting layer.

In the case where the light-emitting layer having the above-described structure includes a plurality of materials, co-evaporation by a vacuum evaporation method can be used, or alternatively an inkjet method, a spin coating method, a dip coating method, or the like with a solution of the materials can be used.

The electron-transport layer 114 is a layer containing a substance having a high electron-transport property. For example, a layer containing a metal complex having a quinoline skeleton or a benzoquinoline skeleton, such as tris(8-quinolinolato)aluminum (abbreviation: Alq), tris(4-methyl- 8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), or the like can be used. Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The dibenzo[f,h]quinoxaline compound described in Embodiment 1 can also be suitably used. The substances mentioned here mainly have an electron mobility of $1\times10^{-6}$ cm$^2$/Vs or more. Note that other than these substances, a substance that has a property of transporting more electrons than holes may be used for the electron-transport layer.

Furthermore, the electron-transport layer 114 is not limited to a single layer and may be a stack of two or more layers containing any of the above substances.

Between the electron-transport layer and the light-emitting layer, a layer that controls transport of electron carriers may be provided. This is a layer formed by addition of a small amount of a substance having a high electron-trapping property to a material having a high electron-transport property as described above, and the layer is capable of adjusting carrier balance by suppressing transport of electron carriers. Such a structure is very effective in preventing a problem (such as a reduction in element lifetime) caused when electrons pass through the light-emitting layer.

Since the dibenzo[,h]quinoxaline compound described in Embodiment 1 has an excellent carrier-transport property, by using the compound as a material of the electron-transport layer 114, a light-emitting element having low driving voltage can be easily provided. Further, since the dibenzo[f,h]quinoxaline compound has a wide band gap and a high triplet level, even when the compound is used as a material of the electron-transport layer 114 adjacent to the light-emitting layer 113 which emits green to red phosphorescence, possibility of deactivation of the excitation energy of the emission center substance is low and a light-emitting element with high emission efficiency which emits green to red light can be easily provided.

In addition, the electron-injection layer 115 may be provided in contact with the second electrode 102 between the electron-transport layer 114 and the second electrode 102. For the electron-injection layer 115, an alkali metal, an alkaline earth metal, or a compound thereof such as lithium fluoride (LiF), cesium fluoride (CsF), or calcium fluoride (CaF$_2$) can be used. For example, a layer that is formed with a substance having an electron-transport property and contains an alkali metal, an alkaline earth metal, or a compound thereof can be used. For example, an Alq layer containing magnesium (Mg) can be used. Note that electron injection from the second electrode 102 is efficiently performed with the use of a layer that is formed with a substance having an electron-transport property and contains an alkali metal or an alkaline earth metal as the electron-injection layer 115, which is preferable.

For the second electrode 102, any of metals, alloys, electrically conductive compounds, and mixtures thereof which have a low work function (specifically, a work function of 3.8 eV or less) or the like can be used. Specific examples of such a cathode material include elements that belong to Groups 1 and 2 of the periodic table, i.e., alkali metals such as lithium (Li) and cesium (Cs), and alkaline earth metals such as magnesium (Mg), calcium (Ca), and strontium (Sr), alloys thereof (e.g., MgAg or ALi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these electrically conductive materials can be formed by a sputtering method, an inkjet method, a spin coating method, or the like.

Further, any of a variety of methods can be used to form the EL layer 103 regardless whether it is a dry process or a wet process. For example, a vacuum evaporation method, an inkjet method, a spin coating method, or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

In the light-emitting element having the above-described structure, current flows due to a potential difference between the first electrode 101 and the second electrode 102, and holes and electrons recombine in the light-emitting layer 113 which contains a substance having a high light-emitting property, so that light is emitted. That is, a light-emitting region is formed in the light-emitting layer 113.

Light emission is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light emission is extracted through the first electrode 101. In the case where only the second electrode 102 is a light-transmitting electrode, light emission is extracted through the second electrode 102. In the case where both the first electrode 101 and the second electrode 102 are light-transmitting electrodes, light emission is extracted through the first electrode 101 and the second electrode 102.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Further, in order that transfer of energy from an exciton generated in the light-emitting layer can be suppressed, preferably, the hole-transport layer and the electron-transport layer which are in direct contact with the light-emitting layer, particularly a carrier-transport layer in contact with a side closer to the light-emitting region in the light-emitting layer 113 is formed with a substance having a wider band gap than the light-emitting substance of the light-emitting layer or the emission center substance included in the light-emitting layer.

In a light-emitting element in this embodiment, when the dibenzo[f,h]quinoxaline compound described in, Embodiment 1 is used for the electron-transport layer, efficient light emission is possible even with the light-emitting substance or the emission center substance that emits phosphorescence; thus, a light-emitting element having high emission efficiency can be obtained. Accordingly, a light-emitting element having higher emission efficiency and lower power consumption can be provided. In addition, a light-emitting element capable of light emission with high color purity can be provided. Further, the dibenzo[f,h]quinoxaline compound described in Embodiment 1 has an excellent carrier-transport property; thus, a light-emitting element having low driving voltage can be provided.

A light-emitting element in this embodiment is preferably fabricated over a substrate of glass, plastic, or the like. As the way of stacking layers over the substrate, layers may be sequentially stacked on the first electrode 101 side or sequentially stacked on the second electrode side. In a light-emitting device, although one light-emitting element may be formed over one substrate, a plurality of light-emitting elements may be formed over one substrate. With a plurality of light-emitting elements as described above formed over one substrate, a lighting device in which elements are separated or a passive-matrix light-emitting device can be manufactured. A light-emitting element may be formed over an electrode electrically connected to a thin film transistor (TFT), for example, which is formed over a substrate of glass, plastic, or the like, so that an active matrix light-emitting device in which the TFT controls the drive of the light-emitting element can be manufactured. Note that there is no particular limitation on the structure of the TFT, which may be a staggered TFT or an inverted staggered TFT. In addition, crystallinity of a semiconductor used for the TFT is not particularly limited either; an amorphous semiconductor or a crystalline semiconductor may be used. In addition, a driver circuit formed in a TFT substrate may be formed with an n-type TFT and a p-type TFT, or with either an n-type TFT or a p-type TFT.

(Embodiment 3)

In this embodiment is described one mode of a light-emitting element having a structure in which a plurality of light-emitting units are stacked (hereinafter, also referred to as stacked-type element), with reference to FIG. 1B. This light-emitting element is a light-emitting element including a plurality of light-emitting units between a first electrode and a second electrode. Each light-emitting unit can have the same structure as the EL layer 103 which is described in Embodiment 2. In other words, the light-emitting element described in Embodiment 2 is a light-emitting element having one light-emitting unit while the light-emitting element described in Embodiment 3 is a light-emitting element having a plurality of light-emitting units.

Figure 1B:
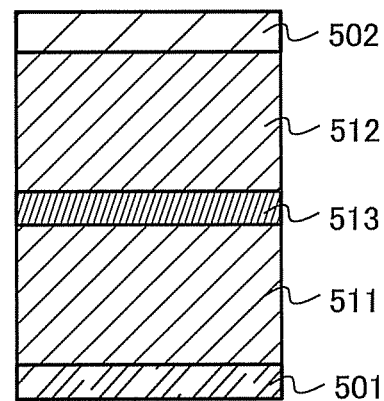

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 respectively correspond to the first electrode 101 and the second electrode 102 in Embodiment 2, and materials described in Embodiment 2 can be used. Further, the structures of the first light-emitting unit 511 and the second light-emitting unit 512 may be the same or different.

The charge generation layer 513 contains a composite material of an organic compound and a metal oxide. This composite material of an organic compound and a metal oxide is the composite material described in Embodiment 2, and contains an organic compound and a metal oxide such as vanadium oxide, molybdenum oxide, or tungsten oxide. As the organic compound, any of a variety of compounds such as aromatic amine compounds, carbazole compounds, aromatic hydrocarbons, and high molecular compounds (oligomers, dendrimers, polymers, or the like) can be used. Note that as the organic compound, the one having a hole mobility of $1\times10^{-6}$ cm$^2$/Vs or more as an organic compound having a hole-transport property is preferably used. Further, other than these substances, any substance that has a property of transporting more holes than electrons may be used. Since a composite of an organic compound and a metal oxide is excellent in carrier-injection property and carrier-transport property, low voltage driving and low current driving can be achieved.

The charge generation layer 513 may be formed in such a way that a layer containing the composite material of an organic compound and a metal oxide is combined with a layer containing another material, for example, with a layer that contains a compound selected from substances having an electron-donating property and a compound having a high electron-transport property. The charge generation layer 513 may be formed in such a way that a layer containing the composite material of an organic compound and a metal oxide is combined with a transparent conductive film.

The charge generation layer 513 provided between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as long as the layer injects electrons into the first light-emitting unit 511 and holes into the second light-emitting unit 512 when a voltage is applied such that the potential of the first electrode is higher than that of the second electrode.

Although the light-emitting element having two light-emitting units is described in this embodiment, the present invention can be similarly applied to a light-emitting element in which three or more light-emitting units are stacked. With a plurality of light-emitting units partitioned by the charge generation layer between a pair of electrodes, as in the light-emitting element according to this embodiment, light emission in a high luminance region can be obtained while current density is kept low; thus, a light-emitting element having a long lifetime can be obtained. Further, in application to lighting devices, a voltage drop due to resistance of an electrode material can be reduced and accordingly light emission in a large area is possible. Moreover, a light-emitting device having low driving voltage and lower power consumption can be obtained.

By making the light-emitting units emit light of different colors from each other, the light-emitting element can provide light emission of a desired color as a whole. For example, by forming a light-emitting element having two light-emitting units such that the emission color of the first light-emitting unit and the emission color of the second light-emitting unit are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white emission can be obtained. Further, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue.

Since a light-emitting element in this embodiment includes the dibenzo[f,h]quinoxaline compound described in Embodiment 1, the light-emitting element can be a light-emitting element having high emission efficiency, a light-emitting element having low driving voltage, or a light-emitting element having a long lifetime. In addition, since light emission with high color purity which is derived from the emission center substance can be obtained from the light-emitting unit including the dibenzo[f,h]quinoxaline compound, color adjustment of the light-emitting element as a whole is easy.

Note that this embodiment can be combined with any of the other embodiments as appropriate.

(Embodiment 4)

In this embodiment, a light-emitting device using a light-emitting element including the dibenzo[f,h]quinoxaline compound described in Embodiment 1 (light-emitting element described in Embodiment 2 or 3) is described.

In this embodiment, the light-emitting device using a light-emitting element including the dibenzo[f,h]quinoxaline compound described in Embodiment 1 is described with reference to FIGS. 2A and 2B. Note that FIG. 2A is a top view of the light-emitting device and FIG. 2B is a cross-sectional view taken along the lines A-B and C-D in FIG. 2A. This light-emitting device includes a driver circuit portion (source line driver circuit) 601, a pixel portion 602, and a driver circuit portion (gate line driver circuit) 603, which are to control light emission of the light-emitting element and illustrated with dotted lines. Moreover, a reference numeral 604 denotes a sealing substrate; 625, a drying agent; 605, a sealing material; and 607, a space surrounded by the sealing material 605.

Reference numeral 608 denotes a wiring for transmitting signals to be inputted into the source line driver circuit 601 and the gate line driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is described with reference to FIG. 2B. The driver circuit portion and the pixel portion are formed over an element substrate 610; the source line driver circuit 601, which is a driver circuit portion, and one of the pixels in the pixel portion 602 are illustrated here.

As the source line driver circuit 601, a CMOS circuit in which an n-channel TFT 623 and a p-channel TFT 624 are combined is formed. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit may not necessarily be formed over the substrate, and the driver circuit can be formed outside, not over the substrate.

The pixel portion 602 includes a plurality of pixels including a switching TFT 611, a current controlling TFT 612, and a first electrode 613 electrically connected to a drain of the current controlling TFT 612. Note that to cover an end portion of the first electrode 613, an insulator 614 is formed, for which a positive type photosensitive acrylic resin film is used here.

In order to improve coverage, the insulator 614 is formed to have a curved surface with curvature at its upper or lower end portion. For example, in the case where positive photosensitive acrylic is used for a material of the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure achieves low wiring resistance, favorable ohmic contact, and a function as an anode.

In addition, the EL layer 616 is formed by any of a variety of methods such as an evaporation method using an evaporation mask, an inkjet method, and a spin coating method. The EL layer 616 includes the dibenzo[f,h]quinoxaline compound described in Embodiment 1. Further, for another material included in the EL layer 616, any of low molecular compounds and high molecular compounds (including oligomers and dendrimers) may be used.

As a material used for the second electrode 617, which is formed over the EL layer 616 and functions as a cathode, a material having a low work function (e.g., Al, Mg, Li, Ca, or an alloy or a compound thereof, such as MgAg, MgIn, or AlLi) is preferably used. In the case where light generated in the EL layer 616 passes through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the EL layer 616, and the second electrode 617. The light-emitting element has the structure described in Embodiment 2. In the light-emitting device of this embodiment, the pixel portion, which includes a plurality of light-emitting elements, may include both the light-emitting element described in Embodiment 1 with the structure described in Embodiment 2 or 3 and a light-emitting element with a structure other than those.

Further, the sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with filler, and may be filled with an inert gas (such as nitrogen or argon), or the sealing material 605.

An epoxy-based resin or glass frit is preferably used for the sealing material 605. It is preferable that such a material do not transmit moisture or oxygen as much as possible. As the sealing substrate 604, a glass substrate, a quartz substrate, or a plastic substrate formed of fiberglass reinforced plastic (FRP), poly(vinyl fluoride) (PVF), polyester, acrylic, or the like can be used.

As described above, the light-emitting device which uses a light-emitting element including the dibenzo[f,h]quinoxaline compound described in Embodiment 1 can be obtained.

The light-emitting device in this embodiment is fabricated using the light-emitting element including the dibenzo[f,h] quinoxaline compound described in Embodiment 1 and thus can have favorable characteristics. Specifically, since the dibenzo[f,h]quinoxaline compound described in Embodiment 1 has a wide energy gap, a high singlet level, and a high triplet level and can suppress energy transfer from a light-emitting substance, a light-emitting element having high emission efficiency can be provided, and accordingly a light-emitting device having reduced power consumption can be provided. In addition, since the dibenzo[f,h]quinoxaline compound has a high carrier-transport property, a light-emitting element having low driving voltage can be provided, and accordingly a light-emitting device having low driving voltage can be provided. Further, since crystallization can be suppressed in a light-emitting element using the dibenzo[f,h]quinoxaline compound described in Embodiment 1, the light-emitting element has a long lifetime, and accordingly a light-emitting device with high reliability can be provided.

Figure 3A:
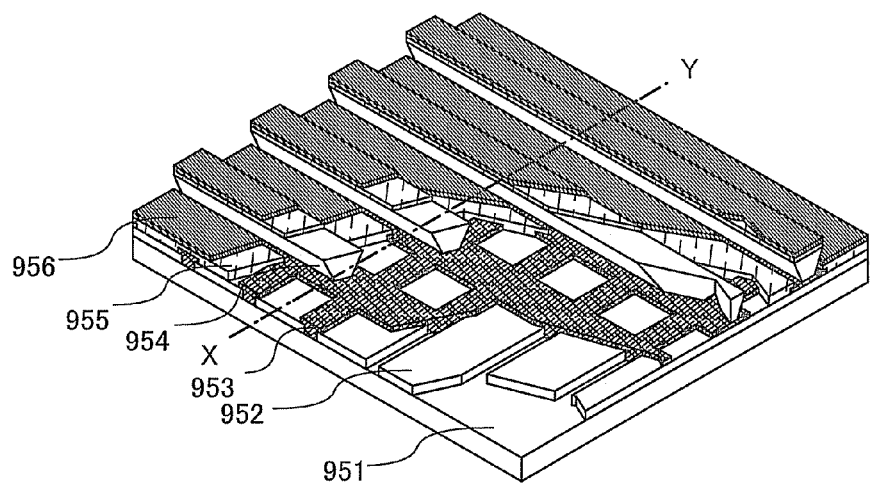
FIGS. 3A and 3B are conceptual diagrams of a passive matrix light-emitting device.
Figure 3B:
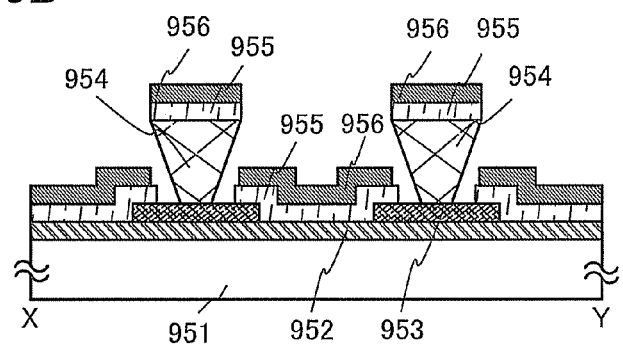

Although an active matrix light-emitting device is described in this embodiment as described above, a passive matrix light-emitting device may be manufactured. FIGS. 3A and 3B illustrate a passive matrix light-emitting device manufactured using the present invention. FIG. 3A is a perspective view of the light-emitting device, and FIG. 3B is a cross-sectional view taken along the line X-Y in FIG. 3A. In FIGS. 3A and 3B, over a substrate 951, an EL layer 955 is provided between an electrode 952 and an electrode 956. An end portion of the electrode 952 is covered with an insulating layer 953. In addition, a partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). The partition layer 954 thus provided can prevent defects in the light-emitting element due to static electricity or the like. The passive matrix light-emitting device can also be driven while power consumption is kept low, by including the light-emitting element described in Embodiment 1 which is capable of operating at low voltage and includes the dibenzo[f,h]quinoxaline compound described in Embodiment 1. In addition, the light-emitting device can be driven while power consumption is kept low, by including the light-emitting element described in Embodiment 1 which includes the dibenzo[f,h]quinoxaline compound described in Embodiment 1 and accordingly has high emission efficiency. Further, the light-emitting device can have high reliability by including the light-emitting element described in Embodiment 1 which includes the dibenzo[f,h]quinoxaline compound described in Embodiment 1.

(Embodiment 5)

Figure 4A:
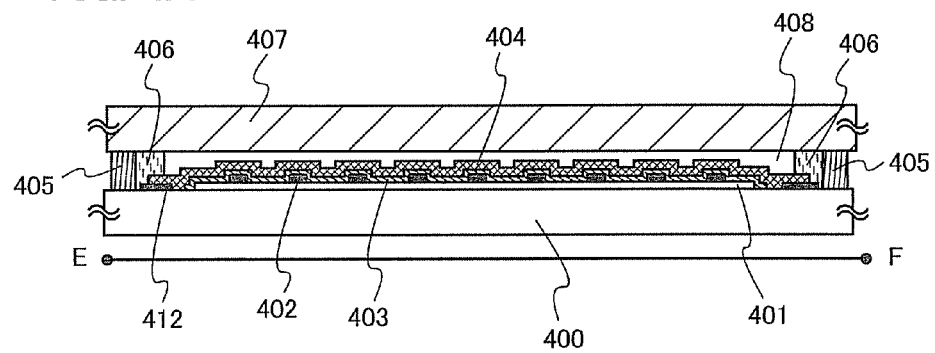
FIGS. 4A and 4B are conceptual diagrams of a lighting device.
Figure 4B:
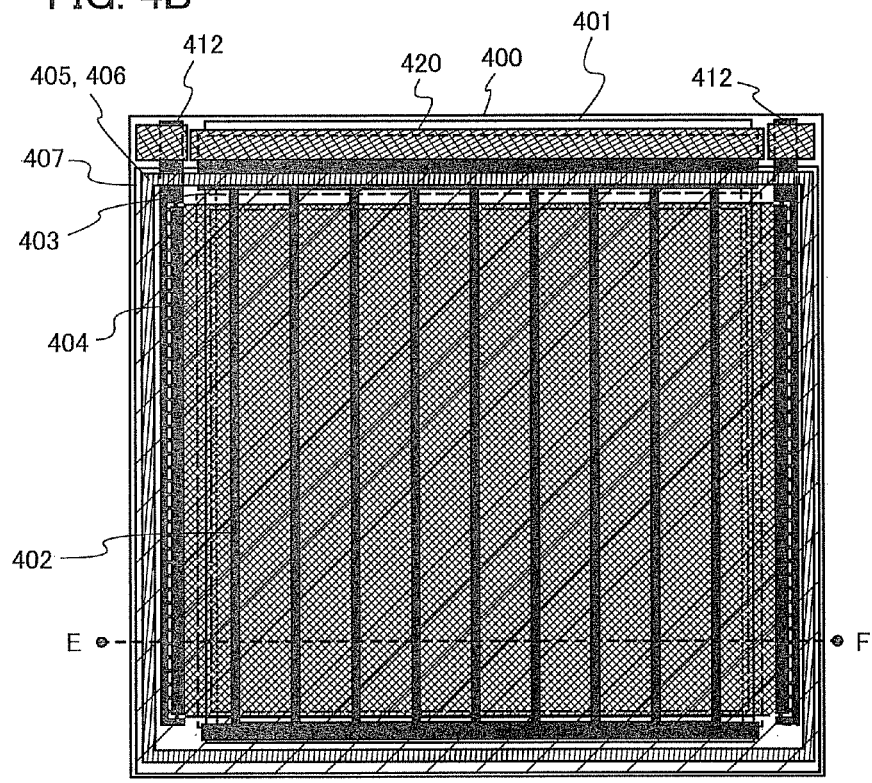

In this embodiment, an example in which a light-emitting element using the dibenzo[f,h]quinoxaline compound described in Embodiment 1 is used for a lighting device is described with reference to FIGS. 4A and 4B. FIG. 4B is a top view of the lighting device, and FIG. 4A is a cross-sectional view taken along the line E-F in FIG. 4B.

In the lighting device in this embodiment, a first electrode 401 is formed over a substrate 400 which is a support and has a light-transmitting property. The first electrode 401 corresponds to the first electrode 101 in Embodiment 3.

An auxiliary electrode 402 is provided over the first electrode 401. Since light emission is extracted through the first electrode 401 side in the example given in this embodiment, the first electrode 401 is formed using a material having a light-transmitting property. The auxiliary electrode 402 is provided in order to compensate for the low conductivity of the material having a light-transmitting property, and has a function of suppressing luminance unevenness in a light emission surface due to voltage drop caused by the high resistance of the first electrode 401. The auxiliary electrode 402 is formed using a material having at least higher conductivity than the material of the first electrode 401, and is preferably formed using a material having high conductivity such as aluminum. Note that surfaces of the auxiliary electrode 402 other than a portion thereof in contact with the first electrode 401 are preferably covered with an insulating layer. This is for suppressing light emission over the upper portion of the auxiliary electrode 402, which cannot be extracted, for reducing a reactive current, and for suppressing a reduction in power efficiency. Note that a pad 412 for applying a voltage to a second electrode 404 may be formed at the same time as the formation of the auxiliary electrode 402.

An EL layer 403 is formed over the first electrode 401 and the auxiliary electrode 402. The EL layer 403 corresponds to a structure of the EL layer 103 in Embodiment 2 or a structure combining the light-emitting units 511 and 512 and the charge generation layer 513. See the explanations of these structures. Note that the EL layer 403 is preferably formed to be slightly larger than the first electrode 401 when seen from above, in which case the EL layer 403 can also serve as an insulating layer that suppresses a short circuit between the first electrode 401 and the second electrode 404.

The second electrode 404 is formed to cover the EL layer 403. The second electrode 404 corresponds to the second electrode 102 in Embodiment 3 and has a similar structure. In this embodiment, it is preferable that the second electrode 404 be formed using a material having high reflectance because light emission is extracted through the first electrode 401 side. In this embodiment, the second electrode 404 is connected to the pad 412, whereby voltage is applied.

As described above, the lighting device described in this embodiment includes a light-emitting element including the first electrode 401, the EL layer 403, and the second electrode 404 (and the auxiliary electrode 402). Since the light-emitting element is a light-emitting element with high emission efficiency, the lighting device in this embodiment can be a lighting device having low power consumption. Further, since the light-emitting element is a light-emitting element having low driving voltage, the lighting device in this embodiment can be a lighting device having low power consumption. Furthermore, since the light-emitting element is a light-emitting element having high reliability, the lighting device in this embodiment can be a lighting device having high reliability.

The light-emitting element having the above structure is fixed to a sealing substrate 407 with sealing materials 405 and 406 and sealing is performed, whereby the lighting device is completed. Note that a space 408 is surrounded by the sealing materials 405 and 406, the sealing substrate 407, and the substrate 400. It is possible to use only either the sealing material 405 or the sealing material 406. In addition, the inner sealing material 406 can be mixed with a desiccant which enables moisture to be adsorbed, increasing reliability.

When parts of the pad 412, the first electrode 401, and the auxiliary electrode 402 are extended to the outside of the sealing materials 405 and 406, the extended parts can serve as external input terminals. An IC chip 420 mounted with a converter or the like may be provided over the external input terminals.

As described above, since the lighting device described in this embodiment includes a light-emitting element including the dibenzo[f,h]quinoxaline compound described in Embodiment 1 as an EL element, the lighting device can be a lighting device having low power consumption. Further, the lighting device can be a lighting device having low driving voltage. Furthermore, the lighting device can be a lighting device having high reliability.

(Embodiment 6)

In this embodiment, examples of electronic devices each including a light-emitting element which uses the dibenzo[f,h]quinoxaline compound described in Embodiment 1 will be described. The light-emitting element which uses the dibenzo[f,h]quinoxaline compound described in Embodiment 1 has high emission efficiency and reduced power consumption. As a result, the electronic devices described in this embodiment can each include a light-emitting portion having reduced power consumption. In addition, the electronic devices can have low driving voltage since the light-emitting element which uses the dibenzo[f,h]quinoxaline compound described in Embodiment 1 has low driving voltage. In addition, the electronic devices in this embodiment can have high reliability since the light-emitting element which uses the dibenzo[f,h]quinoxaline compound described in Embodiment 1 has a long lifetime.

Examples of the electronic device to which the above light-emitting element is applied include television devices (also referred to as TV or television receivers), monitors for computers and the like, cameras such as digital cameras and digital video cameras, digital photo frames, mobile phones (also referred to as cell phones or mobile phone devices), portable game machines, portable information terminals, audio playback devices, large game machines such as pachinko machines, and the like. Specific examples of these electronic devices are given below.

Figure 5A:
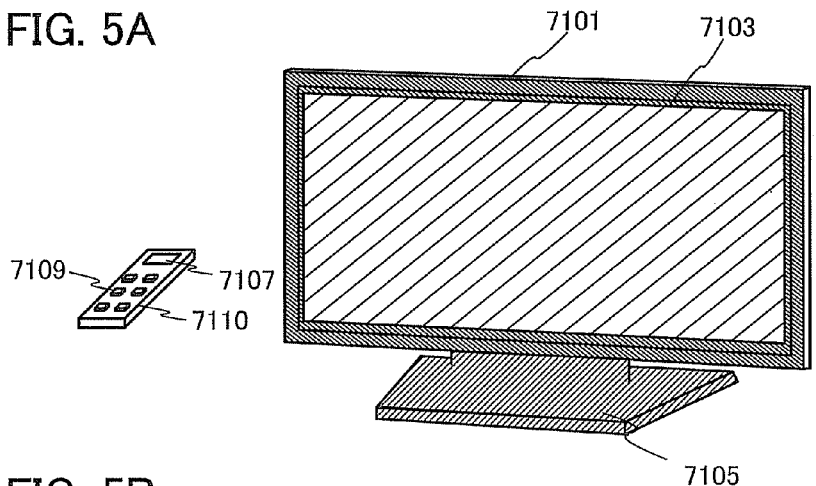
FIGS. 5A to 5D each illustrate an electronic device.

FIG. 5A illustrates an example of a television device. In the television device, a display portion 7103 is incorporated in a housing 7101. In addition, here, the housing 7101 is supported by a stand 7105. The display portion 7103 enables display of images and includes light-emitting elements which use the dibenzo[f,h]quinoxaline compound described in Embodiment 1 and are arranged in a matrix. The light-emitting elements can have high emission efficiency. Further, the light-emitting elements can have low driving voltage. Furthermore, the light-emitting elements can have a long lifetime. Therefore, the television device including the display portion 7103 which is formed using the light-emitting elements can be a television device having reduced power consumption. Further, the television device can be a television device having low driving voltage. Furthermore, the television device can be a television device having high reliability.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

Figure 5B:
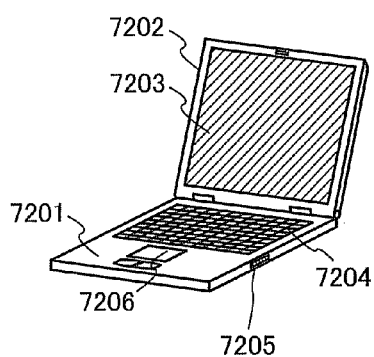

FIG. 5B illustrates a computer, which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203, which include the dibenzo[f,h]quinoxaline compound described in Embodiment 1. The light-emitting elements can have high emission efficiency. Further, the light-emitting elements can have low driving voltage. Furthermore, the light-emitting elements can have a long lifetime. Therefore, the computer including the display portion 7203 which is formed using the light-emitting elements can be a computer having reduced power consumption. Further, the computer can be a computer having low driving voltage. Furthermore, the computer can be a computer having high reliability.

Figure 5C:
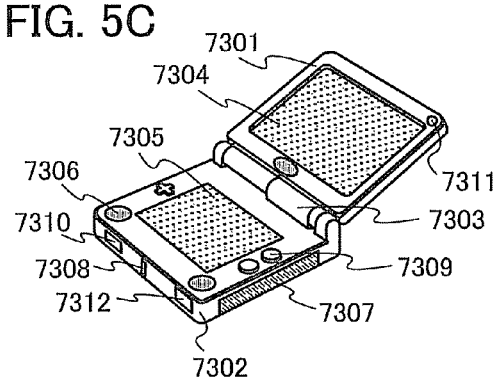

FIG. 5C illustrates a portable game machine having two housings, a housing 7301 and a housing 7302, which are connected with a joint portion 7303 so that the portable game machine can be opened or folded. A display portion 7304 including the light-emitting elements which are described in Embodiment 1 and arranged in a matrix is incorporated in the housing 7301, and a display portion 7305 is incorporated in the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the display portion including light-emitting elements which include the dibenzo[f,h]quinoxaline compound described in Embodiment 1 and are arranged in a matrix is used as at least either the display portion 7304 or the display portion 7305, or both, and the structure can include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above. Since the light-emitting elements used in the display portion 7304 have high emission efficiency, the portable game machine including the above-described display portion 7304 can be a portable, game machine having reduced power consumption. Since the light-emitting elements used in the display portion 7304 each have low driving voltage, the portable game machine can also be a portable game machine having low driving voltage. Furthermore, since the light-emitting elements used in the display portion 7304 each have a long lifetime, the portable game machine can be highly reliable.

Figure 5D:
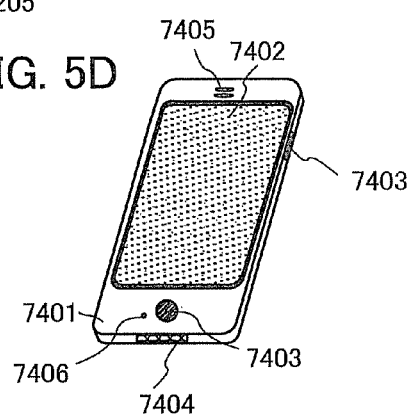

FIG. 5D illustrates an example of a mobile phone. The mobile phone is provided with a display portion 7402 incorporated in a housing 7401, operation buttons 7403, an external connection port 7404, a speaker 7405, a microphone 7406, and the like. Note that the mobile phone 7400 has the display portion 7402 including light-emitting elements which include the dibenzo[f,h]quinoxaline compound described in Embodiment 1 and which are arranged in a matrix. The light-emitting elements can have high emission efficiency. Further, the light-emitting elements can have low driving voltage. Furthermore, the light-emitting elements can have a long lifetime. Therefore, the mobile phone including the display portion 7402 which is formed using the light-emitting elements can be a mobile phone having reduced power consumption. Further, the mobile phone can be a mobile phone having low driving voltage. Furthermore, the mobile phone can be a mobile phone having high reliability.

When the display portion 7402 of the mobile phone illustrated in FIG. 5D is touched with a finger or the like, data can be input into the mobile phone. In this case, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating an e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone, display on the screen of the display portion 7402 can be automatically changed by determining the orientation of the mobile phone (whether the mobile phone is placed horizontally or vertically for a landscape mode or a portrait mode).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Note that the structure described in this embodiment can be combined with any of the structures described in Embodiments 1 to 5 as appropriate.

As described above, the application range of the light-emitting device having the light-emitting element which includes the dibenzo[f,h]quinoxaline compound described in Embodiment 1 is wide so that this light-emitting device can be applied to electronic devices in a variety of fields. By using the light-emitting element which includes the dibenzo[f,h]quinoxaline compound described in Embodiment 1, an electronic device having reduced power consumption and low driving voltage can be obtained.

Figure 6:
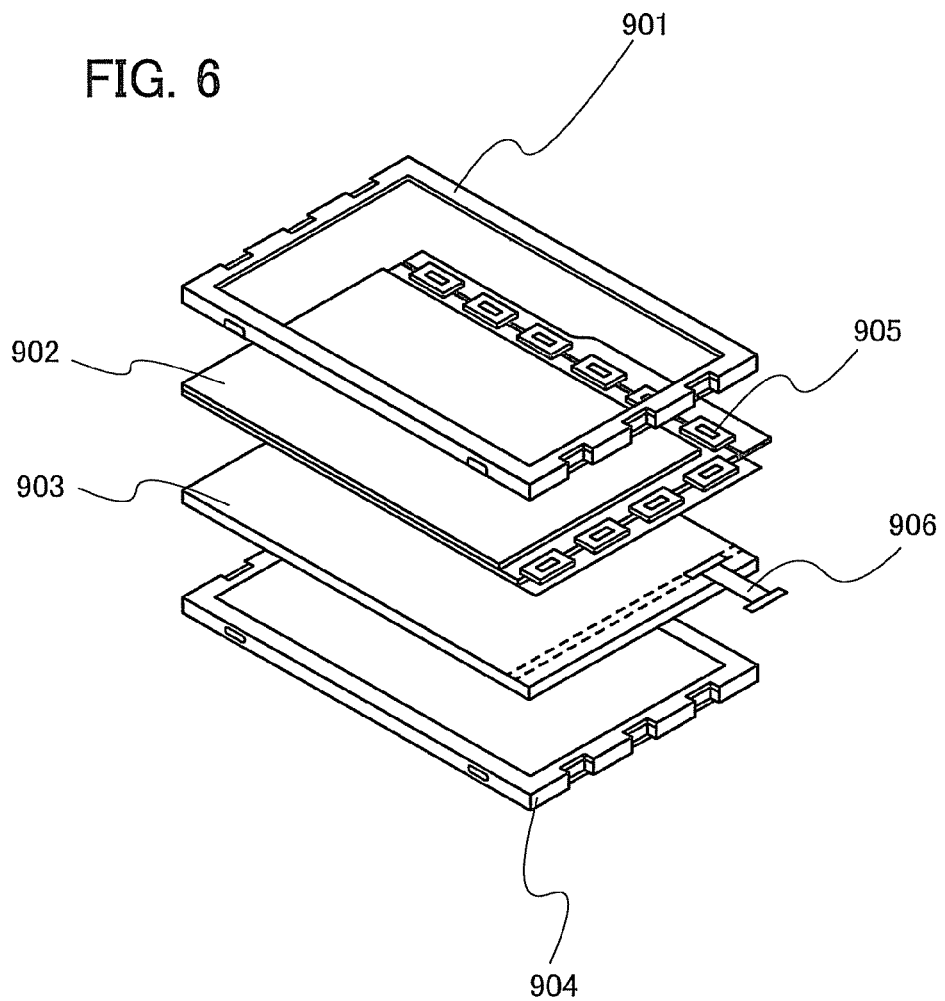
FIG. 6 illustrates an electronic device.

FIG. 6 illustrates an example of a liquid crystal display device using the light-emitting elements including the dibenzo[f,h]quinoxaline compound described in Embodiment 1 for a backlight. The liquid crystal display device illustrated in FIG. 6 includes a housing 901, a liquid crystal layer 902, a backlight unit 903, and a housing 904. The liquid crystal layer 902 is connected to a driver IC 905. The light-emitting element including the dibenzo[f,h]quinoxaline compound described in Embodiment 1 is used in the backlight unit 903, to which current is supplied through a terminal 906.

The light-emitting element including the dibenzo[f,h]quinoxaline compound described in Embodiment 1 is used for the backlight of the liquid crystal display device; thus, the backlight can have reduced power consumption. In addition, the use of the light-emitting element described in Embodiment 2 enables manufacture of a planar-emission lighting device and further a larger-area planar-emission lighting device; therefore, the backlight can be a larger-area backlight, and the liquid crystal display device can also be a larger-area device. Furthermore, the backlight using the light-emitting element described in Embodiment 2 can be thinner than a conventional one; accordingly, the display device can also be thinner.

Figure 7:
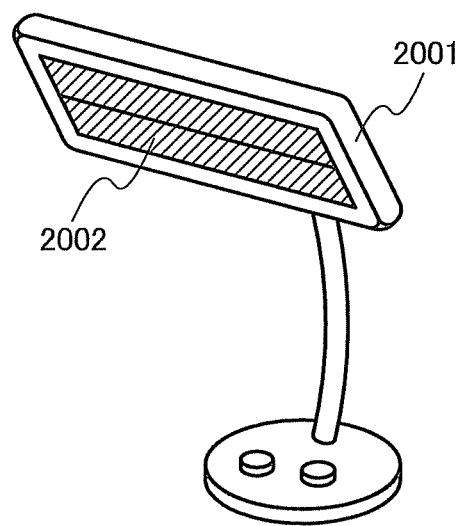
FIG. 7 illustrates a lighting device.

FIG. 7 illustrates an example in which the light-emitting element including the dibenzo[f,h]quinoxaline compound described in Embodiment 1 is used for a table lamp which is a lighting device. The table lamp illustrated in FIG. 7 includes a housing 2001 and a light source 2002, and the light-emitting device described in Embodiment 5 is used for the light source 2002.

Figure 8:
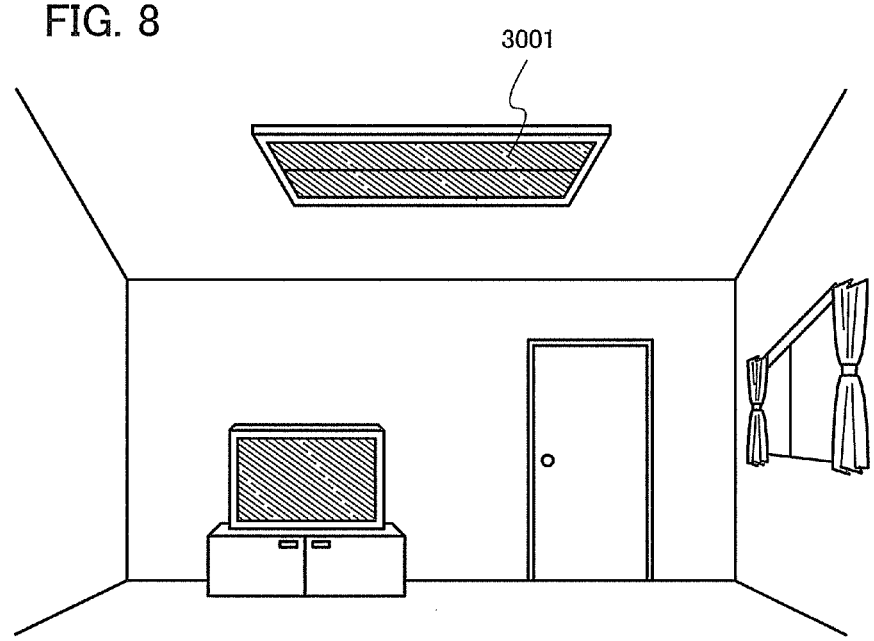
FIG. 8 illustrates a lighting device.

FIG. 8 illustrates an example in which the light-emitting element including the dibenzo[f,h]quinoxaline compound described in Embodiment 1 is used for an indoor lighting device 3001. Since the light-emitting element including the dibenzo[f,h]quinoxaline compound described in Embodiment 1 has reduced power consumption, a lighting device that has reduced power consumption can be obtained. Further, since the light-emitting element including the dibenzo[f,h]quinoxaline compound described in Embodiment 1 can have a large area, the light-emitting element can be used for a large-area lighting device. Furthermore, since the light-emitting element including the dibenzo[f,h]quinoxaline compound described in Embodiment 1 is thin, the light-emitting element can be used for a lighting device having a reduced thickness.

Figure 9:
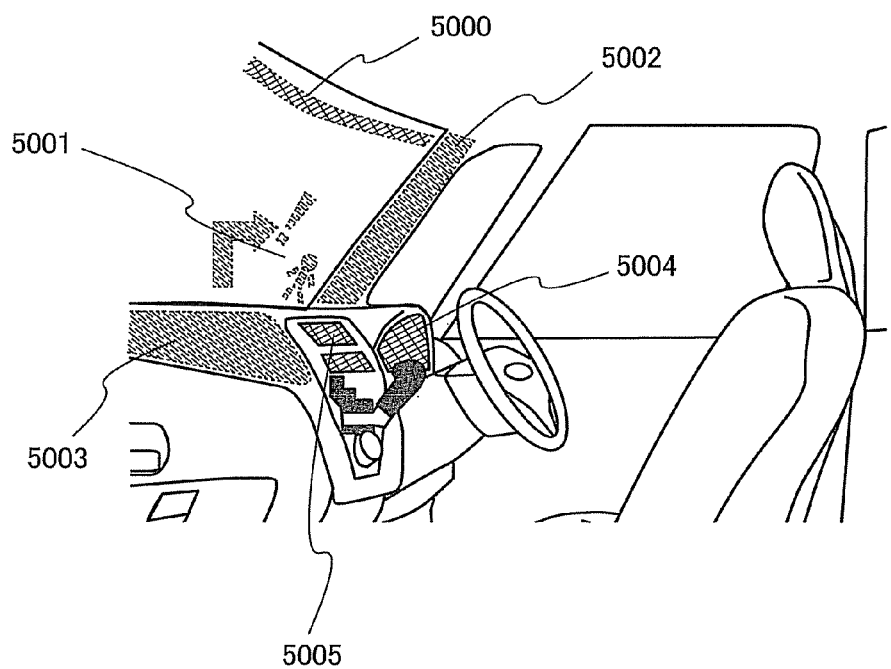
FIG. 9 illustrates car-mounted display devices and lighting devices.

The light-emitting element including the dibenzo[f,h]quinoxaline compound described in Embodiment 1 can also be used for an automobile windshield or an automobile dashboard. FIG. 9 illustrates one mode in which the light-emitting elements described in Embodiment 2 are used for an automobile windshield and an automobile dashboard. Displays 5000 to 5005 each include the light-emitting element including the dibenzo[f,h]quinoxaline compound described in Embodiment 1.

The display 5000 and the display 5001 are display devices which are provided in the automobile windshield and in which the light-emitting elements including the dibenzo[f,h]quinoxaline compound described in Embodiment 1 are incorporated. The light-emitting element including the dibenzo[f,h]quinoxaline compound described in Embodiment 1 can be formed into what is called a see-through display device, through which the opposite side can be seen, by including a first electrode and a second electrode formed of electrodes having light-transmitting properties. Such see-through display devices can be provided even in the windshield of the car, without hindering the vision. Note that in the case where a transistor for driving is provided, a transistor having a light-transmitting property, such as an organic transistor using an organic semiconductor material or a transistor using an oxide semiconductor, is preferably used.

The display 5002 is a display device which is provided in a pillar portion and in which the light-emitting elements including the dibenzo[f,h]quinoxaline compound described in Embodiment 1 are incorporated. The display 5002 can compensate for the view hindered by the pillar portion by showing an image taken by an imaging unit provided in the car body. Similarly, the display 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display 5004 and the display 5005 can provide a variety of kinds of information such as navigation data, a speedometer, a tachometer, a mileage, a fuel meter, a gearshift indicator, and air-condition setting. The content or layout of the display can be changed freely by a user as appropriate. Note that such information can also be shown by the displays 5000 to 5003. The displays 5000 to 5005 can also be used as lighting devices.

A light-emitting element which includes the dibenzo[f,h]quinoxaline compound described in Embodiment 1 can have low driving voltage and low power consumption. Therefore, load on a battery is small even when a number of large screens such as the displays 5000 to 5005 are provided, which provides comfortable use. For that reason, the light-emitting device and the lighting device each of which includes the light-emitting element including the dibenzo[f,h]quinoxaline compound described in Embodiment 1 can be suitably used as an in-vehicle light-emitting device and an in-vehicle lighting device.

Figure 10A:
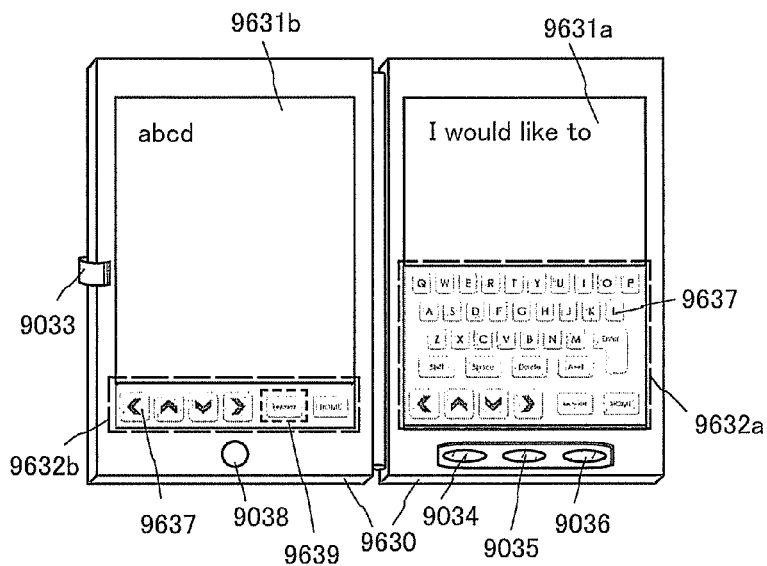
FIGS. 10A to 10C illustrate an electronic device.
Figure 10B:
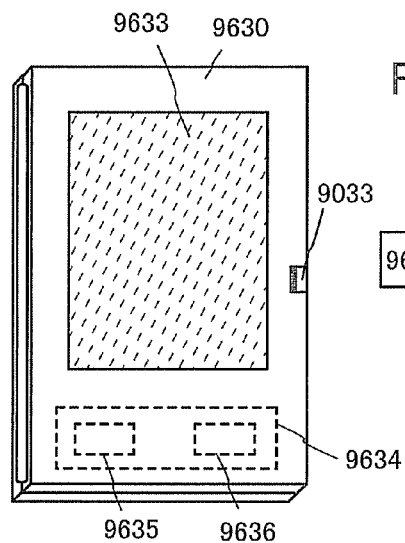

FIGS. 10A and 10B illustrate an example of a foldable tablet. FIG. 10A illustrates the tablet which is unfolded. The tablet includes a housing 9630, a display portion 9631*a*, a display portion 9631*b*, a display mode switch 9034, a power switch 9035, a power-saving mode switch 9036, a clasp 9033, and an operation switch 9038. Note that in the tablet, one or both of the display portion 9631*a* and the display portion 9631*b* is/are formed using a light-emitting device which includes a light-emitting element including the dibenzo[f,h]quinoxaline compound described in Embodiment 1.

Part of the display portion 9631*a* can be a touchscreen region 9632*a* and data can be input when a displayed operation key 9637 is touched. Although half of the display portion 9631*a* has only a display function and the other half has a touchscreen function, one embodiment of the present invention is not limited to the structure. The whole display portion 9631*a* may have a touchscreen function. For example, a keyboard is displayed on the entire region of the display portion 9631*a* so that the display portion 9631*a* is used as a touchscreen; thus, the display portion 9631*b* can be used as a display screen.

Like the display portion 9631*a*, part of the display portion 9631*b* can be a touchscreen region 9632*b*. When a switching button 9639 for showing/hiding a keyboard on the touchscreen is touched with a finger, a stylus, or the like, the keyboard can be displayed on the display portion 9631*b*.

Touch input can be performed in the touchscreen region 9632*a* and the touchscreen region 9632*b* at the same time.

The display mode switch 9034 can switch the display between portrait mode, landscape mode, and the like, and between monochrome display and color display, for example. The power-saving switch 9036 can control display luminance in accordance with the amount of external light in use of the tablet detected by an optical sensor incorporated in the tablet. Another detection device including a sensor for detecting inclination, such as a gyroscope or an acceleration sensor, may be incorporated in the tablet, in addition to the optical sensor.

Although FIG. 10A illustrates an example in which the display portion 9631*a* and the display portion 9631*b* have the same display area, one embodiment of the present invention is not limited to the example. The display portion 9631*a* and the display portion 9631*b* may have different display areas and different display quality. For example, higher definition images may be displayed on one of the display portions 9631*a* and 9631*b*.

FIG. 10B illustrates the tablet which is folded. The tablet includes the housing 9630, a solar cell 9633, a charge and discharge control circuit 9634, a battery 9635, and a DC-to-DC converter 9636. As an example, FIG. 10B illustrates the charge and discharge control circuit 9634 including the battery 9635 and the DC-to-DC converter 9636.

Since the tablet is foldable the housing 9630 can be closed when the tablet is not in use. As a result, the display portion 9631*a* and the display portion 9631*b* can be protected, thereby providing a tablet with high endurance and high reliability for long-term use.

The tablet illustrated in FIGS. 10A and 10B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar cell 9633 provided on a surface of the tablet can supply power to the touchscreen, the display portion, a video signal processing portion, or the like. Note that the solar cell 9633 is preferably provided on one or two surfaces of the housing 9630, in which case the battery 9635 can be charged efficiently.

Figure 10C:
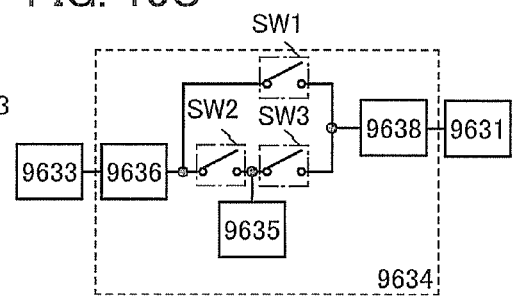

The structure and operation of the charge and discharge control circuit 9634 illustrated in FIG. 10B will be described with reference to a block diagram of FIG. 10C. FIG. 10C illustrates the solar cell 9633, the battery 9635, the DC-to-DC converter 9636, a converter 9638, switches SW1 to SW3, and the display portion 9631. The battery 9635, the DC-to-DC converter 9636, the converter 9638, and the switches SW1 to SW3 correspond to the charge and discharge control circuit 9634 illustrated in FIG. 10B.

First, description is made on an example of the operation in the case where power is generated by the solar cell 9633 with the use of external light. The voltage of the power generated by the solar cell is raised or lowered by the DC-to-DC converter 9636 so as to be voltage for charging the battery 9635. Then, when power supplied from the battery 9635 charged by the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet having the shape illustrated in FIGS. 10A to 10C as long as the display portion 9631 is included.

EXAMPLE 1

Synthesis Example 1

In this example will be described a method of synthesizing 2-(6-phenyldibenzothiophen-4-yl)dibenzo[f,h]quinoxaline (abbreviation: 2DBTDBq-IV), the dibenzo[f,h]quinoxaline compound represented by Structural Formula (101) in Embodiment 1. The structural formula of 2DBTDBq-IV is shown below.

(101)

Step 1: Synthesis Method of 2-(6-Phenyldibenzothiophen-4-yl)dibenzo[f,h]quinoxaline (Abbreviation: 2DBTDBq-IV)

A mixture of 0.58 g (2.1 mmol) of 2-chlorodibenzo[f,h]quinoxaline, 0.58 g (1.9 mmol) of 4-phenyldibenzothiophene-6-boronic acid, 50 mg (80 mol) of tetrakis(triphenylphosphine)palladium(0), 50 mL of toluene, 3 mL of ethanol, and 4 mL of a 2 mol/L potassium carbonate aqueous solution was degassed while being stirred under a reduced pressure in a 200-mL three-neck flask; then, the mixture was stirred while being heated at 85° C. under a nitrogen atmosphere for 7 hours to cause a reaction.

After the reaction, this reaction mixture was filtered, and the residue was washed with water and toluene in this order. The obtained residue was dissolved into hot toluene, and filtered through Celite (produced by Wako Pure Chemical Industries, Ltd., Catalog No. 531-16855), silica gel, and Florisil (produced by Wako Pure Chemical Industries, Ltd., Catalog No. 540-00135) in this order. The obtained filtrate was purified by silica gel column chromatography. At this time, toluene was used as a developing solvent for the chromatography. The obtained fraction was concentrated, and toluene was added thereto. The mixture was washed with ultrasonic waves and a resulting solid was collected, so that the objective substance was obtained as 0.51 mg of a pale yellow powder in a yield of 55%. A reaction scheme of the above synthesis method is illustrated in Reaction Scheme (a-1).

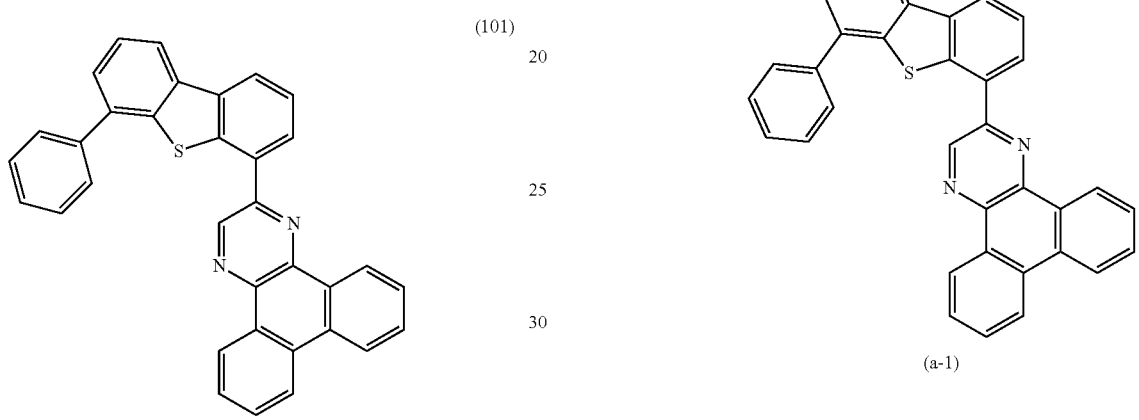

(a-1)

The Rf values of the objective substance and 2-chlorodibenzo[f,h]quinoxaline were respectively 0.31 and 0.55, which were found by silica gel thin layer chromatography (TLC) (with a developing solvent of ethyl acetate and hexane in a ratio of 1:10).

The obtained compound in Step 1 was subjected to a nuclear magnetic resonance (NMR) measurement. The measurement data are shown below.

$^1$H NMR (CDCl$_3$, 300 MHz): δ(ppm)=7.54-7.85 (m, 10H), 7.92-7.95 (m, 2H), 8.26 (dd, J=7.2 Hz, J=1.5 Hz, 1H), 8.40-8.44 (m, 2H), 8.64-8.68 (m, 2H), 9.26-9.29 (m, 1H), 9.58 (dd, J=6.9 Hz, J=0.9 Hz, 1H), 9.69 (s, 1H).

Figure 11A:
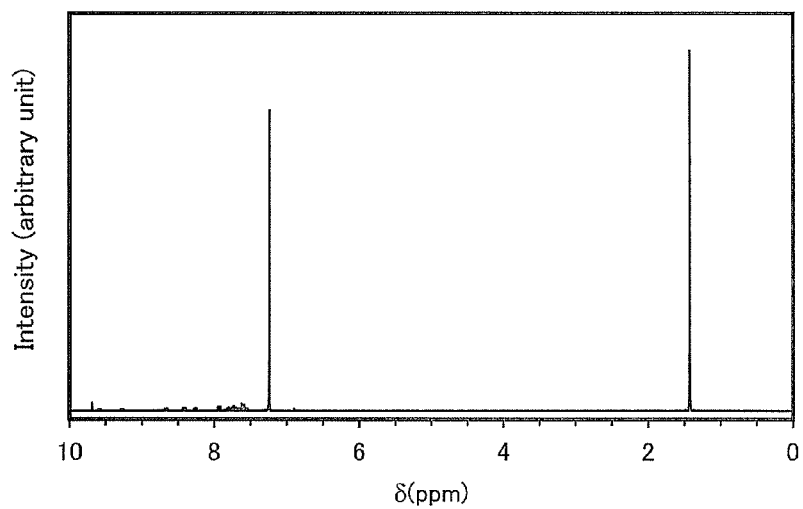
FIGS. 11A and 11B show $^1$H NMR charts of 2-(6-phenyldibenzothiophen-4-yl)dibenzo[f,h]quinoxaline (abbreviation: 2DBTDBq-IV).
Figure 11B:
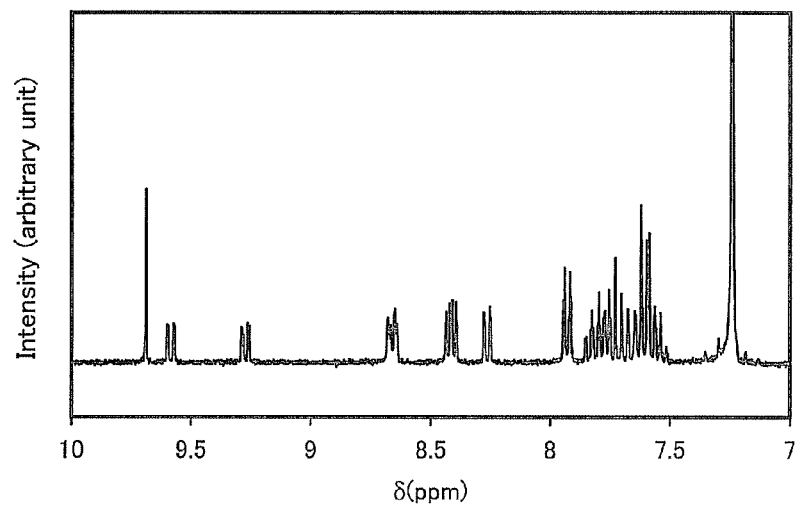

FIGS. 11A and 11B show $^1$H NMR charts. Note that FIG. 11B is an enlarged chart of FIG. 11A. The measurement results confirmed that 2DBTDBq-IV (abbreviation) that was the objective substance was obtained.

Figure 12A:
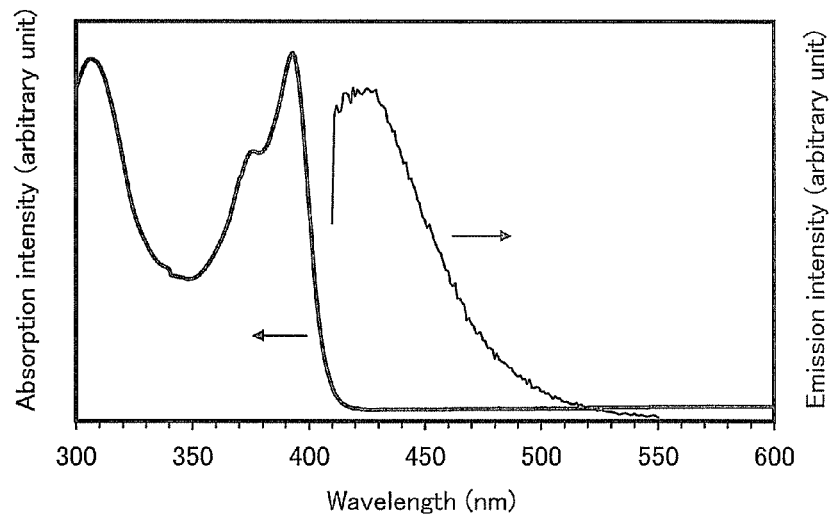
FIGS. 12A and 12B show absorption spectra and emission spectra of 2DBTDBq-IV.
Figure 12B:
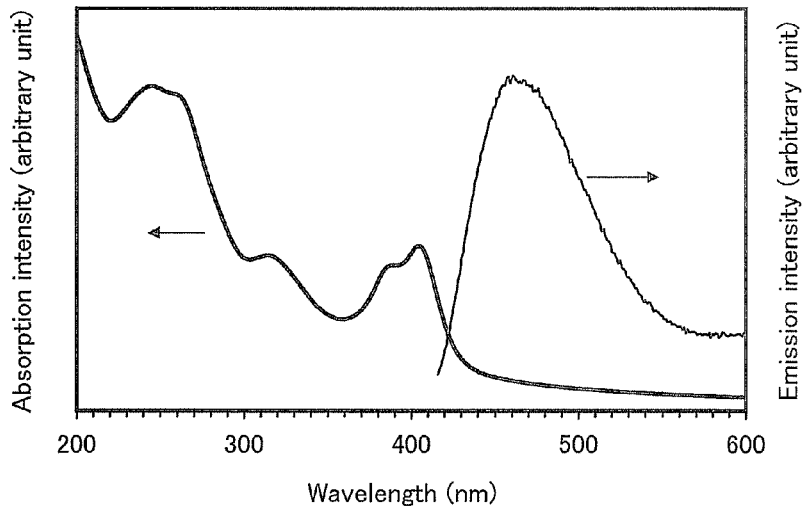

FIG. 12A shows an absorption and emission spectra of 2DBTDBq-IV in a toluene solution of 2DBTDBq-IV, and FIG. 12B shows an absorption and emission spectra of a thin film of 2DBTDBq-IV. The absorption spectra were measured with an ultraviolet-visible spectrophotometer (V-550, manufactured by JASCO Corporation). The measurements were performed with samples prepared in such a manner that the solution was put in a quartz cell and the thin film was obtained by evaporation onto a quartz substrate. The absorption spectrum of 2DBTDBq-IV in the solution of 2DBTDBq-IV was obtained by subtracting the absorption spectra of the quartz cell and toluene from those of quartz and the solution, and the absorption spectrum of the thin film was obtained by subtracting the absorption spectrum of the quartz substrate from those of the quartz substrate and the thin film. In FIGS. 12A and 12B, the horizontal axis indicates the wavelength (nm) and the vertical axis indicates the intensity (arbitrary unit). In the case of the toluene solution, an absorption peak was observed at around 393 nm, and an emission wavelength peak was 425 nm (at an excitation wavelength of 395 nm). In the case of the thin film, absorption peaks were observed at around 405 nm, 388 nm, 316 nm, 260 nm, and 244 nm, and an emission wavelength peak was 461 nm (at an excitation wavelength of 404 nm).

Further, optical characteristics of a thin film of 2DBTDBq-IV were measured (the measuring instrument was AC-2 produced by Riken Keiki, Co., Ltd.). Note that the measurement of optical characteristics of the thin film was carried out as follows.

The value of the HOMO level was obtained by conversion of the value of the ionization potential measured with a photoelectron spectrometer (AC-2, produced by Riken Keiki Co., Ltd.) in the air into a negative value. The value of the LUMO level was obtained in such a manner that the absorption edge, which was obtained from Tauc plot with an assumption of direct transition using data on the absorption spectrum of the thin film, was regarded as an optical energy gap and was added to the value of the HOMO level.

From the measurement results of the optical characteristics of the thin film, the HOMO level, the LUMO level, and the band gap (Bg) of 2DBTDBq-IV were respectively calculated at −5.59 eV, −2.66 eV, and 2.93 eV.

Electrochemical characteristics (oxidation and reduction characteristics) of a solution of 2DBTDBq-IV were measured by cyclic voltammetry (CV). Note that an electrochemical analyzer (ALS model 600A or 600C, produced by BAS Inc.) was used for the measurements.

In the measurements, the potential of a working electrode with respect to the reference electrode was changed within an appropriate range, so that the oxidation peak potential and the reduction peak potential were each obtained. From the obtained peak potentials, the HOMO and LUMO levels of 2DBTDBq-IV were respectively calculated at −6.22 eV and −2.99 eV.

The calculations of the HOMO and LUMO levels using CV measurement are detailed below.

For a solution for the CV measurements, dehydrated N,N-dimethylformamide (DMF, produced by Sigma-Aldrich Inc., 99.8%, catalog No. 22705-6) was used as a solvent, and tetra-n-butylammonium perchlorate (n-$Bu_4NClO_4$, produced by Tokyo Chemical Industry Co., Ltd., catalog No. T0836), which was a supporting electrolyte, was dissolved in the solvent such that the concentration was 100 mmol/L. Further, the object to be measured was also dissolved in the solvent such that the concentration was 2 mmol/L.

A platinum electrode (a PTE platinum electrode, produced by BAS Inc.) was used as the working electrode; a platinum electrode (a VC-3 Pt counter electrode (5 cm), produced by BAS Inc.) was used as an auxiliary electrode; and an Ag/$Ag^+$ electrode (an RE5 nonaqueous solvent reference electrode, produced by BAS Inc.) was used as the reference electrode. Note that the measurements were conducted at room temperature (20° C. to 25° C.). The scan rates for the CV measurements were uniformly set to 0.1 V/s.

In the measurement of the oxidation characteristics, one cycle was scanning in which the potential of the working electrode with respect to the reference electrode was changed from −0.39 V to 1.50 V and then changed from 1.50 V to −0.39 V.

In the measurements of the reduction characteristics, one cycle was scanning in which the potential of the working electrode with respect to the reference electrode was changed from −1.23 V to −2.10 V and then changed from −2.10 V to −1.23 V.

The HOMO level was obtained by subtraction of a half-wave potential $E_{1/2}$ (an intermediate potential between $E_{pa}$ and $E_{pc}$), which was calculated from the oxidation peak potential $E_{pa}$ and reduction peak potential $E_{pc}$ obtained in the measurement of the oxidation characteristics of 2DBTDBq-IV, from the potential energy of the reference electrode, which was used, with respect to the vacuum level.

The oxidation peak potential $E_{pa}$ was 1.35 V and the reduction peak potential $E_{pc}$ was 1.20 V according to the measurement of the oxidation characteristics of 2DBTDBq-IV. The half-wave potential $E_{1/2}$ was therefore 1.28 V, and since the potential energy of the reference electrode, which was used in the measurements, with respect to the vacuum level is −4.94 eV, the HOMO level of the solution of 2DBTDBq-IV can be calculated as follows: −4.94−1.28=−6.22 eV.

The LUMO level was obtained by subtraction of a half-wave potential $E_{1/2}$ (an intermediate potential between $E_{pa}$ and $E_{pc}$), which was calculated from the reduction peak potential $E_{pc}$ and oxidation peak potential $E_{pa}$ obtained in the measurement of the reduction characteristics of 2DBTDBq-IV, from the potential energy of the reference electrode, which was used, with respect to the vacuum level.

The reduction peak potential $E_{pc}$ was −2.00 V and the oxidation peak potential $E_{pa}$ was −1.90 V according to the measurement of the reduction characteristics of 2DBTDBq-IV. The half-wave potential $E_{1/2}$ was therefore −1.95 V, and since the potential energy of the reference electrode, which was used in the measurements, with respect to the vacuum level is −4.94 eV, the LUMO level of the solution of 2DBTDBq-IV can be calculated as follows: −4.94−(−1.95)=−2.99 eV.

Note that the potential energy of the reference electrode (Ag/$Ag^+$ electrode) with respect to the vacuum level corresponds to the Fermi level of the Ag/$Ag^+$ electrode, and should be calculated from a value obtained by measuring a substance whose potential energy with respect to the vacuum level is known, with the use of the reference electrode (Ag/$Ag^+$ electrode).

How the potential energy (eV) of the reference electrode (Ag/$Ag^+$ electrode), which was used in this example, with respect to the vacuum level is calculated will be specifically described. It is known that the oxidation-reduction potential of ferrocene in methanol is +0.610 V (vs. SHE) with respect to the standard hydrogen electrode (reference: Christian R. Goldsmith et al., *J. Am. Chem. Soc.*, Vol. 124, No. 1, pp. 83-96, 2002). In contrast, using the reference electrode used in this example, the oxidation-reduction potential of ferrocene in methanol was calculated at +0.11 V (vs. Ag/$Ag^+$). Thus, it was found that the potential energy of this reference electrode was lower than that of the standard hydrogen electrode by 0.50 [eV].

Here, it is known that the potential energy of the standard hydrogen electrode with respect to the vacuum level is −4.44 eV (reference: Toshihiro Ohnishi and Tamami Koyama, *High molecular EL material*, Kyoritsu shuppan, pp. 64-67). Therefore, the potential energy of the reference electrode, which was used in this example, with respect to the vacuum level can be calculated as follows: −4.44−0.50=−4.94 [eV].

EXAMPLE 2

In this example, a light-emitting element of one embodiment of the present invention will be described with reference to FIG. 1A. Chemical formulae of materials used in this example are shown below.

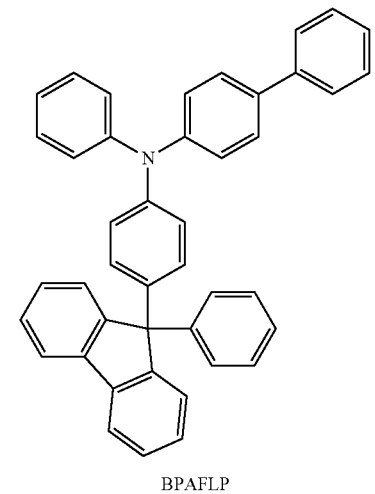

BPAFLP

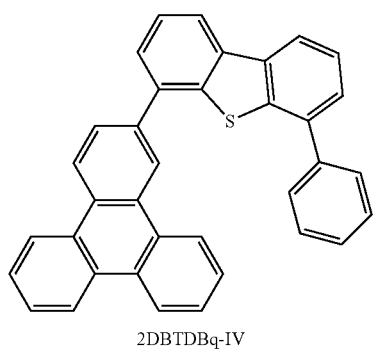

2DBTDBq-IV

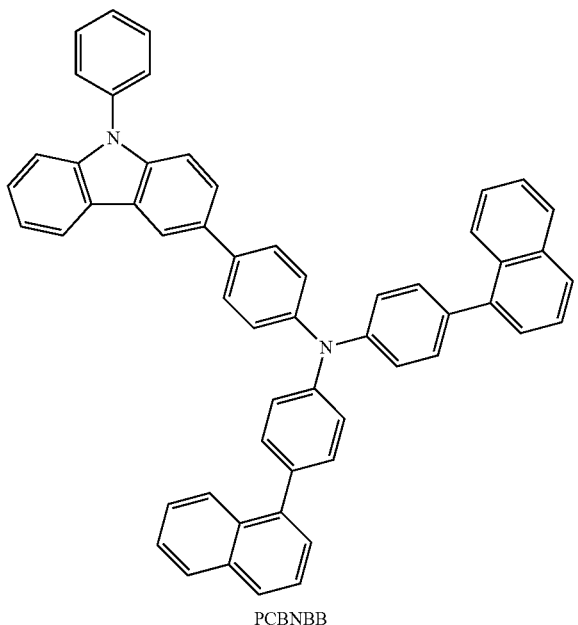

PCBNBB

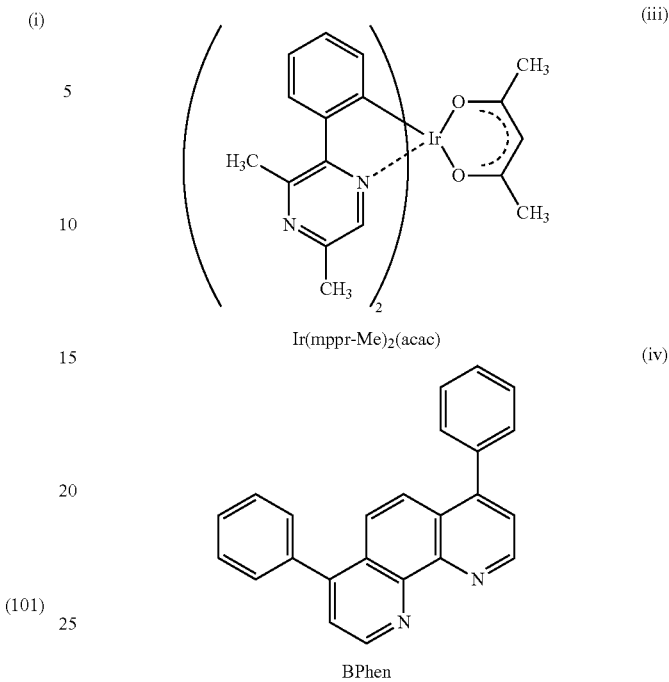

Ir(mppr-Me)₂(acac)

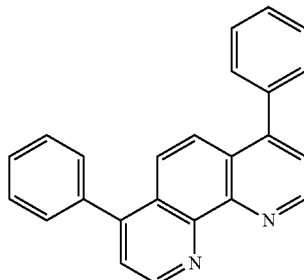

BPhen

A method of manufacturing Light-emitting Element 1 of this example will be described below.

(Light-emitting Element 1)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 is an electrode that functions as an anode of the light-emitting element.

Next, as pretreatment for forming the light-emitting element over the substrate, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to about $10^{-4}$ Pa. After that, over the first electrode 101, 4-phenyl-4'-(9-phenylfluoren-9-yl)triphenylamine (abbreviation: BPAFLP) and molybdenum(VI) oxide were co-evaporated by an evaporation method using resistance heating, so that the hole-injection layer 111 was formed. The thickness of the hole-injection layer 111 was set to 40 nm, and the weight ratio of BPAFLP to molybdenum oxide was adjusted to 4:2 (=BPAFLP:molybdenum oxide). Note that the co-evaporation method refers to an evaporation method in which evaporation is carried out from a plurality of evaporation sources at the same time in one treatment chamber.

Next, a film of 4-phenyl-4'-(9-phenylfluoren-9-yl)triphenylamine (abbreviation: BPAFLP) was formed to a thickness of 20 nm over the hole-injection layer 111 to form the hole-transport layer 112.

Further, 2-(6-phenyldibenzothiophen-4-yl)dibenzo[f,h]quinoxaline (abbreviation: 2DBTDBq-IV) synthesized in Example 1, 4,4'-di(1-naphthyl)-4"-(9-phenyl-9H-carbazol-3-yl)triphenylamine (abbreviation: PCBNBB), and (acetylacetonato)bis(3,5-dimethyl-2-phenylpyrazinato)iridium (III) (abbreviation: [Ir(mppr-Me)$_2$(acac)]) were co-evaporated to form the light-emitting layer 113 over the hole-transport layer 112. The weight ratio of 2DBTDBq-IV to PCBNBB and [Ir(mppr-Me)$_2$(acac)] was adjusted to 1:0.25:0.06 (=2DBTDBq-IV:PCBNBB[Ir(mppr-Me)$_2$(acac)]). The thickness of the light-emitting layer 113 was set to 40 nm.

Further, a film of 2DBTDBq-IV was formed to a thickness of 10 nm over the light-emitting layer 113 and a film of bathophenanthroline (abbreviation: BPhen) was formed to a thickness of 20 nm, so that the electron-transport layer 114 was formed.

Then, a film of lithium fluoride (LiF) was formed to a thickness of 1 nm over the electron-transport layer 114 to form the electron-injection layer 115.

Lastly, an aluminum film was formed by evaporation to a thickness of 200 nm as the second electrode 102 functioning as a cathode. Thus, Light-emitting Element 1 of this example was fabricated.

Note that in all the above evaporation steps, evaporation was performed by a resistance-heating method.

An element structure of Light-emitting Element 1 obtained as described above is shown in Table 1.

TABLE 1

| First Electrode | Hole injection layer | Hole transport layer | Light-emitting layer | Electron transport layer | Electron injection layer | Second electrode |
|---|---|---|---|---|---|---|
| ITSO 110 nm | BPAFLP:MoOx (=4:2) 40 nm | BPAFLP 20 nm | 2DBTDBqIV:PGBNBB: [Ir(mppr-Me)$_2$(acac)] (=1:0.25:0.06) 40 nm | 2DBTDBqIV 10 nm | BPhen 20 nm | LiF 1 nm | Al 200 nm |

In a glove box containing a nitrogen atmosphere, Light-emitting Element 1 was sealed with a glass substrate so as not to be exposed to the air. Then, operation characteristics of the light-emitting element were measured. Note that the measurement was carried out at room temperature (in an atmosphere kept at 25° C.).

Figure 13:
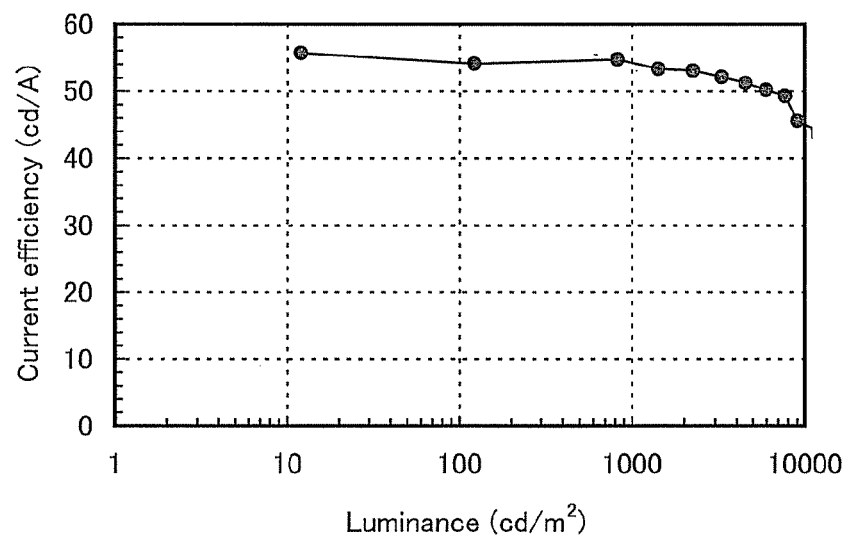
FIG. 13 is a graph showing luminance-current efficiency characteristics of Light-emitting Element 1.
Figure 14:
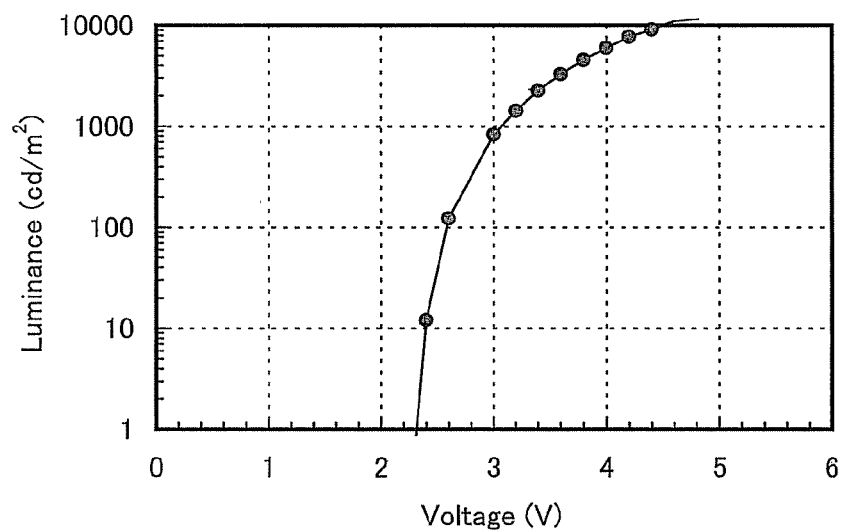
FIG. 14 is a graph showing voltage-luminance characteristics of Light-emitting Element 1.
Figure 15:
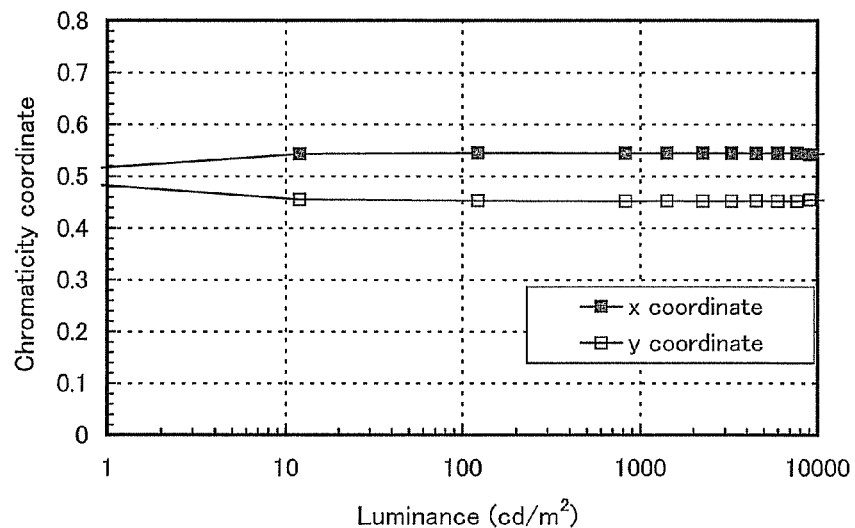
FIG. 15 is a graph showing luminance-chromaticity coordinate characteristics of Light-emitting Element 1.
Figure 16:
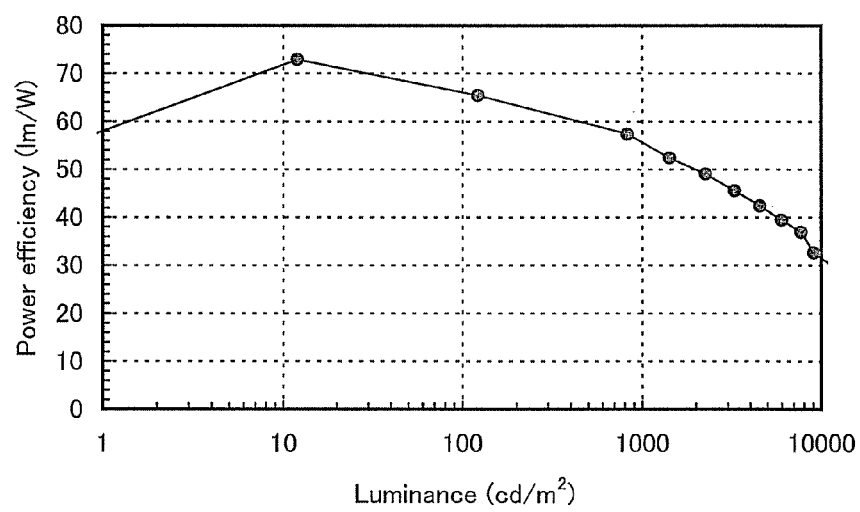
FIG. 16 is a graph showing luminance-power efficiency characteristics of Light-emitting Element 1.

FIG. 13 shows luminance-current efficiency characteristics of Light-emitting Element 1. In FIG. 13, the horizontal axis indicates luminance (cd/m$^2$) and the vertical axis indicates current efficiency (cd/A). FIG. 14 shows voltage-luminance characteristics of Light-emitting Element 1. In FIG. 14, the horizontal axis indicates voltage (V) and the vertical axis indicates luminance (cd/m$^2$). FIG. 15 shows luminance-chromaticity coordinate characteristics of Light-emitting Element 1. In FIG. 15, the horizontal axis indicates luminance (cd/m$^2$) and the vertical axis indicates chromaticity coordinate (the x-coordinate or the y-coordinate). In addition, FIG. 16 shows luminance-power efficiency characteristics of Light-emitting Element 1. In FIG. 16, the horizontal axis indicates luminance (cd/m$^2$) and the vertical axis indicates power efficiency (lm/W). Table 2 shows voltage (V), current density (mA/cm$^2$), CIE chromaticity coordinates (x, y), luminance (cd/m$^2$), current efficiency (cd/A), and external quantum efficiency (%) of the light-emitting element at a luminance of around 1000 cd/m$^2$.

Figure 17:
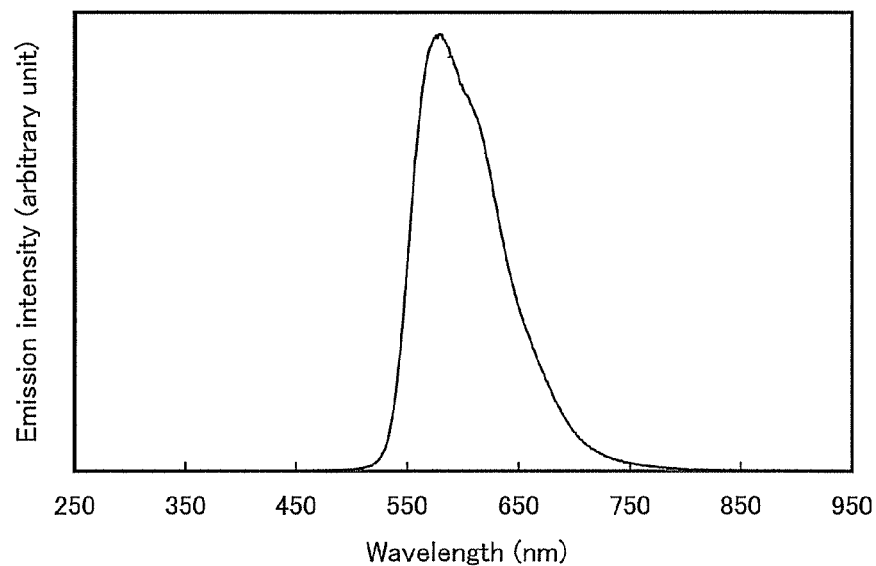
FIG. 17 shows an emission spectrum of Light-emitting Element 1.

FIG. 17 shows an emission spectrum of Light-emitting Element 1 which was obtained when a current of 0.1 mA was made to flow in Light-emitting Element 1. In FIG. 17, the horizontal axis indicates wavelength (nm) and the vertical axis indicates emission intensity (arbitrary unit). As shown in FIG. 17 and Table 2, the CIE chromaticity coordinates of Light-emitting Element 1 were (x, y)=(0.54, 0.45) at a luminance of around 1000 cd/m$^2$. It was found that Light-emitting Element 1 exhibited light emission from [Ir(mppr-Me)$_2$(acac)]. This revealed that 2DBTDBq-IV, which is the dibenzo[f,h]quinoxaline compound according to one embodiment of the present invention, has a T$_1$ level which enables an orange phosphorescent material to sufficiently emit light. Accordingly, it was found that 2DBTDBq-IV can be used as a host material for orange phosphorescent materials.

FIG. 14 and Table 2 revealed that Light-emitting Element 1 is driven at low voltage. Light-emitting Element 1 includes 2DBTDBq-IV, which is the dibenzo[f,h]quinoxaline compound according to one embodiment of the present invention, as the host material in the light-emitting layer and the material in the electron-transport layer. Accordingly, the light-emitting element can be driven at low voltage.

FIG. 13, FIG. 16, and Table 2 show that the current efficiency, the power efficiency, and the external quantum efficiency of Light-emitting Element 1 are high. In 2DBTDBq-IV, the dibenzo[f,h]quinoxaline compound, a dibenzothiophene ring is bonded to a dibenzo[f,h]quinoxaline ring, and a decrease in a band gap or a T$_1$ level due to crystallization is unlikely to occur. Thus, the orange phosphorescent substance [Ir(mppr-Me)$_2$(acac)] can be effectively excited, so that an element having high emission efficiency can be obtained.

As shown in FIG. 15, Light-emitting Element 1 shows substantially no change in color over a range from low luminance to high luminance. It can be said from this result that Light-emitting Element 1 is an element having excellent carrier balance.

Figure 18:
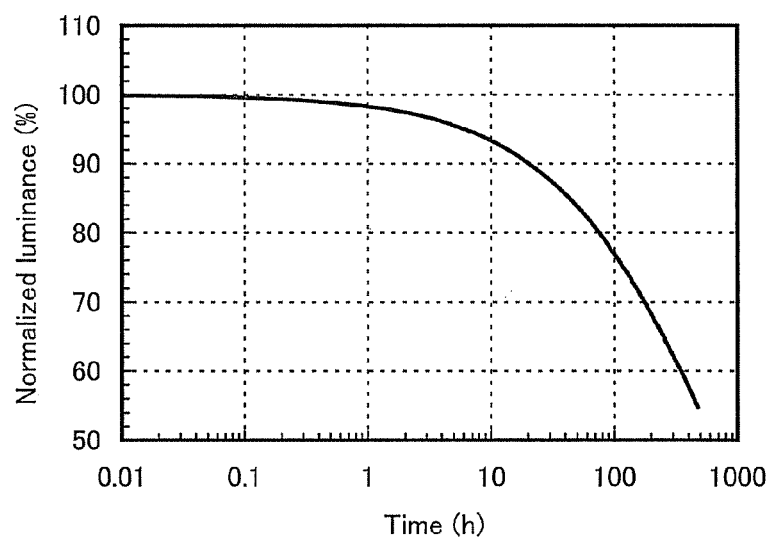
FIG. 18 is a graph showing time-normalized luminance characteristics of Light-emitting Element 1.

Next, Light-emitting Element 1 was subjected to a reliability test. The results of the reliability test are shown in FIG. 18. In FIG. 18, the vertical axis indicates normalized luminance (%) with an initial luminance of 100% and the horizontal axis indicates driving time (h) of the element. In the reliability test, the light-emitting element of this example was driven at room temperature under the conditions where the initial luminance was set to 5000 cd/m$^2$ and the current density was constant. FIG. 18 shows that Light-emitting Element 1 kept 55% of the initial luminance after driving for 480 hours. These results of the reliability test revealed that Light-emitting Element 1 has a long lifetime.

TABLE 2

| | Voltage (V) | Current density (mA/cm$^2$) | Chromaticity (x) | Chromaticity (y) | Luminance (cd/m$^2$) | Current efficiency (cd/A) | External quantum efficiency (%) |
|---|---|---|---|---|---|---|---|
| Light-emitting element 1 | 3.0 | 1.5 | 0.54 | 0.45 | 827 | 55 | 20 |

As described above, by the use of 2DBTDBq-IV synthesized in Example 1 as the host material in the light-emitting layer and the material in the electron-transport layer, the light-emitting element can have low driving voltage, high emission efficiency, and a long lifetime.

EXAMPLE 3

In this example, triplet (T₁) levels of the dibenzo[f,h]quinoxaline compounds represented by Structural Formulae (101), (120), (130), and (133), each of which is one embodiment of the present invention represented by General Formula (G1) in Embodiment 1, were calculated. The four structural formulae are shown below.

(101)
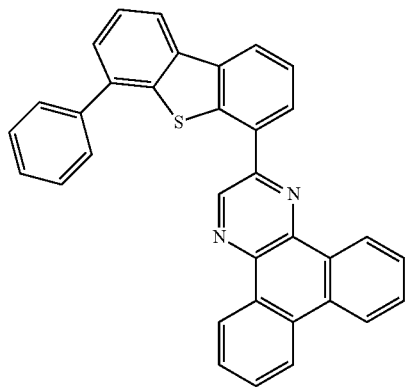

(120)
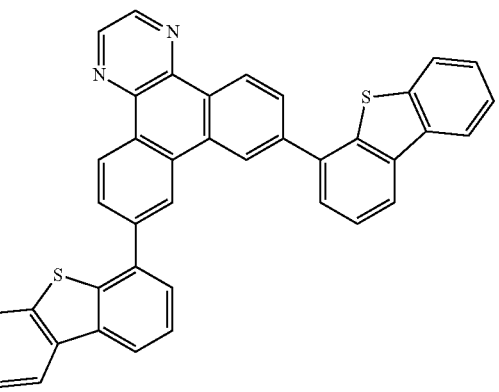

(130)
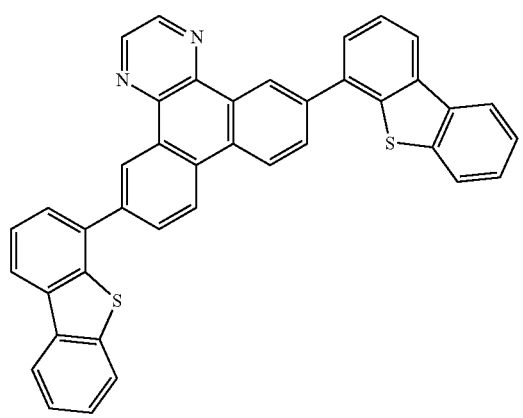

(133)
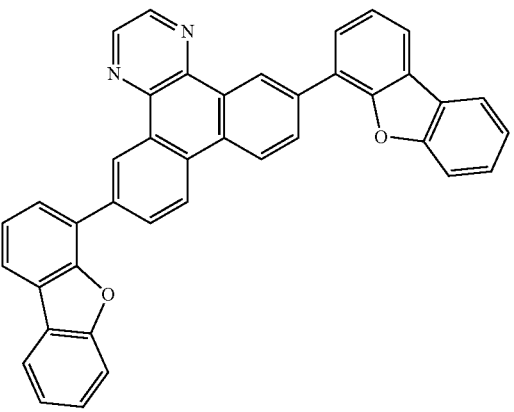

The calculating method is as follows. Note that Gaussian 09 was used as a quantum chemistry computational program. A high performance computer (Altix 4700 manufactured by SGI Japan, Ltd.) was used for the calculations.

First, the most stable structure in the singlet state was calculated using the density functional theory. As a basis function, 6-311 (a basis function of a triple-split valence basis set using three contraction functions for each valence orbital) was applied to all the atoms. By the above basis function, for example, is to 3s orbitals are considered in the case of hydrogen atoms, while is to 4s and 2p to 4p orbitals are considered in the case of carbon atoms. Furthermore, to improve calculation accuracy, the p function and the d function as polarization basis sets were added to hydrogen atoms and atoms other than hydrogen atoms, respectively. As a functional, B3LYP was used.

Next, the most stable structure in the triplet state was calculated. The energy of the triplet level was calculated from an energy difference between the most stable structures in the singlet state and in the triplet state. As a basis function, 6-311G (d, p) was used. As a functional, B3LYP was used.

The calculation results are shown in Table 3.

TABLE 3

| Structural Formula | Name of Compound (abbr.) | unit: [eV] T₁ |
|---|---|---|
| (101) | 2DBTDBq-IV | 2.39 |
| (120) | 7,10DBT2DBq-II | 2.58 |
| (130) | 6,11DBT2DBq-II | 2.54 |
| (133) | 6,11DBF2DBq-II | 2.45 |

The above results show that the dibenzo[f,h]quinoxaline compounds according to one embodiment of the present invention have high triplet levels.

This application is based on Japanese Patent Application serial no. 2011-242246 filed with Japan Patent Office on Nov. 4, 2011, the entire contents of which are hereby incorporated by reference.

What is claimed is:

1. A dibenzo[f,h]quinoxaline compound comprising a dibenzo[f,h]quinoxaline skeleton,
    wherein a dibenzothiophene skeleton is directly bonded to the dibenzo[f,h]quinoxaline skeleton, and
    wherein the dibenzothiophene skeleton is a substituted or unsubstituted dibenzothiophen-4-yl group.
2. A light-emitting element comprising the dibenzo[f,h]quinoxaline compound according to claim 1.

3. A light-emitting element comprising a light-emitting layer between an anode and a cathode, wherein the light-emitting layer comprises a light-emitting substance and the dibenzo[f,h]quinoxaline compound according to claim 1.

4. A light-emitting element comprising a light-emitting layer between an anode and a cathode, the light-emitting layer comprising a light-emitting substance, an electron-transport compound, and a hole-transport compound,
wherein the electron-transport compound is the dibenzo[f,h]quinoxaline compound according to claim 1, and
wherein the hole-transport compound has a higher hole-transport property than the electron-transport compound and comprises a carbazole skeleton, a triarylamine skeleton, a dibenzothiophene skeleton, or a dibenzofuran skeleton.

5. A light-emitting device comprising the light-emitting element according to claim 2.

6. An electronic device comprising the light-emitting device according to claim 5.

7. A lighting device comprising the light-emitting device according to claim 5.

8. A dibenzo[f,h]quinoxaline compound represented by General Formula (G1), (G1)

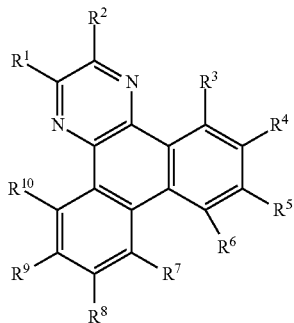

wherein any one of $R^1$ to $R^{10}$ represents a first substituted or unsubstituted dibenzothiophen-4-yl group, and the others of $R^1$ to $R^{10}$ separately represent any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a second substituted or unsubstituted dibenzothiophen-4-yl group, and a second substituted or unsubstituted dibenzofuran-4-yl group.

9. The dibenzo[f,h]quinoxaline compound according to claim 8,
wherein the first substituted or unsubstituted dibenzothiophen-4-yl group is represented by General Formula (G1-1), (G1-1)

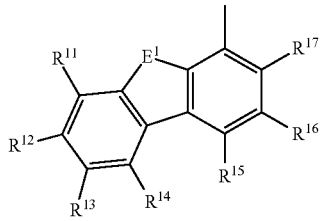

wherein $E^1$ represents sulfur, and $R^{11}$ to $R^{17}$ separately represent any of hydrogen, an alkyl group having 1 to 6 carbon atoms, a substituted or unsubstituted phenyl group, and a substituted or unsubstituted biphenyl group,
wherein the second substituted or unsubstituted dibenzothiophen-4-yl group is represented by General Formula (G1-2), and (G1-2)

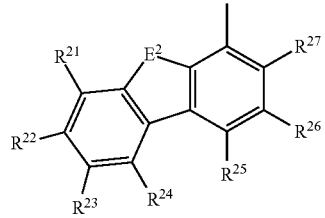

wherein $E^2$ represents sulfur, and $R^{21}$ to $R^{27}$ separately represent any of hydrogen, an alkyl group having 1 to 6 carbon atoms, a substituted or unsubstituted phenyl group, and a substituted or unsubstituted biphenyl group.

10. The dibenzo[f,h]quinoxaline compound according to claim 8, wherein the dibenzo[f,h]quinoxaline compound is represented by General Formula (G3), (G3)

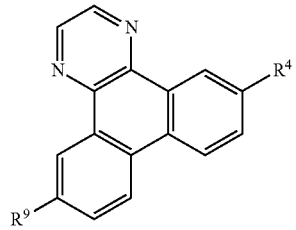

wherein one of $R^4$ and $R^9$ represents a first substituted or unsubstituted dibenzothiophen-4-yl group, and the other of $R^4$ and $R^9$ represents any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a second substituted or unsubstituted dibenzothiophen-4-yl group, and a second substituted or unsubstituted dibenzofuran-4-yl group.

11. The dibenzo[f,h]quinoxaline compound according to claim 8, wherein the dibenzo[f,h]quinoxaline compound is represented by General Formula (G4), (G4)

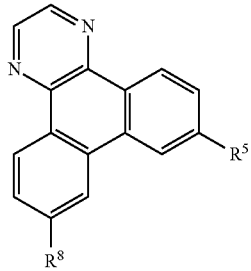

wherein one of $R^5$ and $R^8$ represents a first substituted or unsubstituted dibenzothiophen-4-yl group, and the other of $R^5$ and $R^8$ represents any of hydrogen, an alkyl group having 1 to 6 carbon atoms, a substituted or unsubstituted phenyl group, a substituted or unsubstituted biphenyl group, a substituted or unsubstituted naphthyl group, a substituted or unsubstituted phenanthryl group, a substituted or unsubstituted triphenylenyl group, a second substituted or unsubstituted dibenzothiophen-4-yl group, and a second substituted or unsubstituted dibenzofuran-4-yl group.

12. The dibenzo[f,h]quinoxaline compound according to claim 8, wherein the dibenzo[f,h]quinoxaline compound is represented by General Formula (G5),

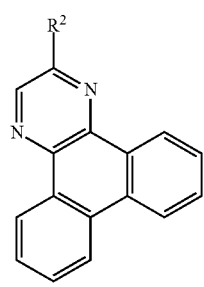

(G5)

wherein $R^2$ represents a substituted or unsubstituted dibenzothiophen-4-yl group.

13. The dibenzo[f,h]quinoxaline compound according to claim 9,
wherein:
the group represented by General Formula (G1-1) is a group represented by General Formula (G2-1) and the group represented by General Formula (G1-2) is a group represented by General Formula (G2-2),

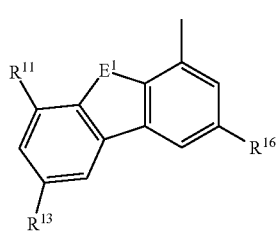

(G2-1)

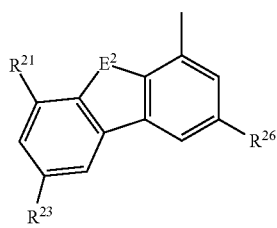

(G2-2)

$E^1$ represents sulfur, and $R^{11}$, $R^{13}$, and $R^{16}$ separately represent any of hydrogen, an alkyl group having 1 to 6 carbon atoms, a substituted or unsubstituted phenyl group, and a substituted or unsubstituted biphenyl group, and $E^2$ represents sulfur or oxygen, and $R^{21}$, $R^{23}$, and $R^{26}$ separately represent any of hydrogen, an alkyl group having 1 to 6 carbon atoms, a substituted or unsubstituted phenyl group, and a substituted or unsubstituted biphenyl group.

14. The dibenzo[f,h]quinoxaline compound according to claim 8, wherein the dibenzo[f,h]quinoxaline compound is represented by Structural Formula (100)

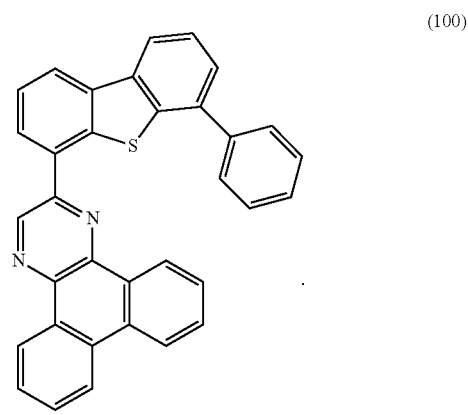 [SMILES: c1ccc(-c2cccc3c2sc2c(-c4cnc5c6ccccc6c6ccccc6c5n4)cccc23)cc1]

(100)

15. A light-emitting element comprising the dibenzo[f,h] quinoxaline compound according to claim 8.

16. A light-emitting element comprising a light-emitting layer between an anode and a cathode, wherein the light-emitting layer comprises a light-emitting substance and the dibenzo[f,h]quinoxaline compound according to claim 8.

17. A light-emitting element comprising a light-emitting layer between an anode and a cathode, the light-emitting layer comprising a light-emitting substance, an electron-transport compound, and a hole-transport compound,
wherein the electron-transport compound is the dibenzo[f, h]quinoxaline compound according to claim 8, and
wherein the hole-transport compound has a higher hole-transport property than the electron-transport compound and comprises a carbazole skeleton, a triarylamine skeleton, a dibenzothiophene skeleton, or a dibenzofuran skeleton.

18. A light-emitting device comprising the light-emitting element according to claim 15.

19. An electronic device comprising the light-emitting device according to claim 18.

20. A lighting device comprising the light-emitting device according to claim 18.

* * * * *